US012810980B2

(12) United States Patent
Norgeot et al.

(10) Patent No.: US 12,810,980 B2
(45) Date of Patent: Nov. 24, 2026

(54) GRAPHICAL USER INTERFACE FOR ARTIFACT INSPECTION USING AN ARTIFICIAL INTELLIGENCE (AI) MODEL

(71) Applicant: Qualified Health PBC, San Carlos, CA (US)

(72) Inventors: Beau Norgeot, Los Gatos, CA (US); Chinmay Belthangady, Castro Valley, CA (US); Justin Norden, Menlo Park, CA (US); Aman Sinha, Palo Alto, CA (US); Nidhi Ramamurthy, San Jose, CA (US); Maxim Rabinovich, Somerville, MA (US); Ripple Goyal, Santa Clara, CA (US); Vidyasagar Ranganaboina, Sunnyvale, CA (US); Komal Rao, Santa Clara, CA (US); Dmitriy Timokhin, Mountain View, CA (US); Neha Pandey, Fremont, CA (US); Saber Bahranifard, Belmont, CA (US); Sadhana Ravoori, Redwood City, CA (US); Harvineet Singh, San Carlos, CA (US)

(73) Assignee: Qualified Health PBC, San Carlos, CA (US)

( * ) Notice: Subject to any disclaimer, the term of this patent is extended or adjusted under 35 U.S.C. 154(b) by 0 days.

(21) Appl. No.: 19/405,605

(22) Filed: Dec. 2, 2025

(65) Prior Publication Data

US 2026/0155219 A1 Jun. 4, 2026

Related U.S. Application Data

(60) Provisional application No. 63/822,067, filed on Jun. 11, 2025, provisional application No. 63/735,162,
(Continued)

(51) Int. Cl.
*G16H 15/00* (2018.01)
*G06F 8/34* (2018.01)
*G16H 10/60* (2018.01)

(52) U.S. Cl.
CPC ............... *G16H 15/00* (2018.01); *G06F 8/34* (2013.01); *G16H 10/60* (2018.01)

(58) Field of Classification Search
None
See application file for complete search history.

(56) References Cited

U.S. PATENT DOCUMENTS 11,789,837 B1 * 10/2023 Jain ..................... G06F 11/3006 709/224
2009/0192822 A1 * 7/2009 Regulapati ............. G16H 50/70 707/E17.014
(Continued)

OTHER PUBLICATIONS

Gebreab et al., "LLM-Based Framework for Administrative Task Automation in Healthcare," 2024 12th InternationalSymposium on Digital Forensics and Security (ISDFS), San Antonio, TX, USA, 2024, pp. 1-7. (2024).
(Continued)

*Primary Examiner* — Devin C Hein
*Assistant Examiner* — Vincent C Ilagan
(74) *Attorney, Agent, or Firm* — Ashurst Perkins Coie US LLP

(57) ABSTRACT

Operations for providing artifact inspection using an artificial intelligence (AI) model include displaying an AI-generated electronic artifact created by an AI system using an input comprising user data associated with a subject from a data source and a set of instructions. The AI-generated electronic artifact can indicate a user status for the subject created using the user data. The status identifies a condition for the subject. The operations also include displaying, on the graphical user interface, a confidence evaluation gener-
(Continued)

ated by the AI system. The confidence evaluation includes a numerical value related to the accuracy or quality of the status or treatment of the subject. The operations also include displaying a portion of the medical data that the AI system used for the AI-generated electronic artifact to enable inspection of the accuracy of the AI-generated electronic artifact.

20 Claims, 24 Drawing Sheets

Related U.S. Application Data filed on Dec. 17, 2024, provisional application No. 63/727,622, filed on Dec. 3, 2024.

(56) References Cited

U.S. PATENT DOCUMENTS

| | | | | |
|---|---|---|---|---|
| 2015/0142473 | A1* | 5/2015 | Sethumadhavan | G16H 50/70 705/3 |
| 2021/0059616 | A1* | 3/2021 | Abrol | A61B 5/0022 |
| 2022/0004713 | A1 | 1/2022 | Han et al. | |
| 2024/0331816 | A1 | 10/2024 | Agassi et al. | |
| 2024/0404687 | A1 | 12/2024 | Bell et al. | |
| 2025/0123820 | A1 | 4/2025 | Khan et al. | |
| 2025/0272499 | A1 | 8/2025 | Neagovici | |
| 2025/0335818 | A1 | 10/2025 | Maurice et al. | |
| 2025/0378967 | A1* | 12/2025 | Gnanasambandam | G16H 50/70 |
| 2026/0111816 | A1 | 4/2026 | Balasubramanian et al. | |
| 2026/0120025 | A1 | 4/2026 | Tyo et al. | |
| 2026/0133771 | A1 | 5/2026 | Rathakrishnan | |

OTHER PUBLICATIONS

Musumeci et al., "LLM Based Multi-Agent Generation of Semi-structured Documents from Semantic Templates in the Public Administration Domain," arXiv:2402.14871v1 [cs.CL]. (Feb. 21, 2024).

Sree et al., "Retrieval-Augmented Generation based Large Language Model Chatbot for Improving Diagnosis for Physical and Mental Health," 2024 6th Int'l Conf on Electrical, Control and Instrumentation Eng'r (ICECIE), (2024).

* cited by examiner

400

< Back to Marketplace

Utilization Review

An automated system that drafts evidence based notes from physician notes, labs, medical records etc. – ensuring accurate capture of payer requirements and correct inpatient classification to prevent costly and time-consuming adjudication.

Search | Sort By

402

| Encounter ID ↓ | Generated ↓ | Patient Sex | Insurance | Physician Classification | QH Classification | QH Confidence level |
|---|---|---|---|---|---|---|
| ENC-2034-AB12 | Dec 12, 2024 | Male | Medicare | Observation | Observation | 70% |
| ENC-4578-CD34 | Dec 12, 2024 | Male | Medicaid | In-Patient | In-Patient | 80% |
| ENC-9812-EF56 | Dec 12, 2024 | Female | Private | Observation | Observation | 92% |
| ENC-1123-GH56 | Dec 11, 2024 | Male | Medicaid | Observation | In-Patient | 75% |
| ENC-3345-IJ90 | Dec 09, 2024 | Female | Private | Observation | Observation | 79% |
| ENC-3356-IJ90 | Dec 08, 2024 | Female | Medicare | In-Patient | In-Patient | 88% |
| ENC-3345-IJ90 | Dec 05, 2024 | Female | Medicaid | Observation | Observation | 60% |
| ENC-3345-IJ90 | Dec 05, 2024 | Female | Private | In-Patient | Observation | 74% |
| ENC-3345-IJ90 | Dec 05, 2024 | Male | Medicare | In-Patient | In-Patient | 82% |
| ENC-3345-IJ90 | Dec 05, 2024 | Male | Medicaid | In-Patient | In-Patient | 91% |
| ENC-3345-IJ90 | Dec 05, 2024 | Male | Medicaid | In-Patient | In-Patient | 76% |
| ENC-3345-IJ90 | Dec 05, 2024 | Female | Medicare | Observation | Observation | 83% |

*FIG. 4A*

(I)

summarize this patient note in a few sentences
Patient Name: Jane Smith Date: 12/1/2030 MRN: 654321 DOB: 05/15/1990
Provider: Dr. Johnson
S: Subjective
Chief Complaint: "I have been experiencing severe headaches and nausea." History of Present Illness: The patient describes the headaches as throbbing and located primarily on one side of the head. Nausea accompanies the headaches but no vomiting. Denies visual disturbances or aura. Past ...

(II)

Draft an email to a hospital leader about the following information
Patient Sarah Johnson (DOB: 04/15/1978, SSN: 123-45-6789) reported discrimination at Acme Medical Center due to her Hispanic ethnicity and Buddhist religious beliefs. The doctor's notes form Dr. William Chen contain no indication of this

*FIG. 11D*

GRAPHICAL USER INTERFACE FOR ARTIFACT INSPECTION USING AN ARTIFICIAL INTELLIGENCE (AI) MODEL

CROSS-REFERENCE TO RELATED APPLICATIONS

This application claims priority to and benefit from to U.S. Provisional Application No. 63/727,622, titled "System and Method for Intelligent Workflow Design, Evolution, and Deployment Using Natural Language Processing," filed Dec. 3, 2024, U.S. Provisional Application No. 63/735,162, titled "System and Method for Real-Time Obfuscation and De-obfuscation of Sensitive Information in Large Language Model Communications," filed Dec. 17, 2024, and U.S. Provisional Application No. 63/822,067, titled "Artifact Source and Lineage Management and Inspection," filed Jun. 11, 2025, the contents of each of which are incorporated herein by reference in their entireties. This application is related to U.S. patent application Ser. No. 19/405,554, titled "Artifact Source and Lineage Management and Inspection," filed concurrently with this application, the contents of which are incorporated herein by reference in their entirety.

BACKGROUND

In the healthcare industry, documentation is important for providing continuity of care, enhancing patient safety, supporting clinical decision-making, and enabling efficient healthcare management and administration. Healthcare artifacts can include, for example, medical histories and records, patient charts, treatment plans, diagnostic reports, prescription records, and insurance claims. An important part of healthcare management also includes documentation related to utilization reviews. Utilization reviews can involve evaluation processes used to assess the necessity, appropriateness, and efficiency of medical services and treatments by healthcare providers to ensure optimal patient outcomes and cost-effective care. Healthcare documentation can generally be complex because it involves detailed and accurate recording of diverse and extensive patient information, medical histories, treatments, and regulatory compliance requirements, all of which must be meticulously maintained and updated to ensure efficient and accurate patient care.

BRIEF DESCRIPTION OF THE DRAWINGS

Reference will now be made, by way of example, to the accompanying drawings, which show example embodiments of the present application, and in which:

FIGS. 11A through 11E illustrate processes and interfaces for obfuscation and de-obfuscation of sensitive information, in accordance with some implementations of the present technology.

Figure 1:
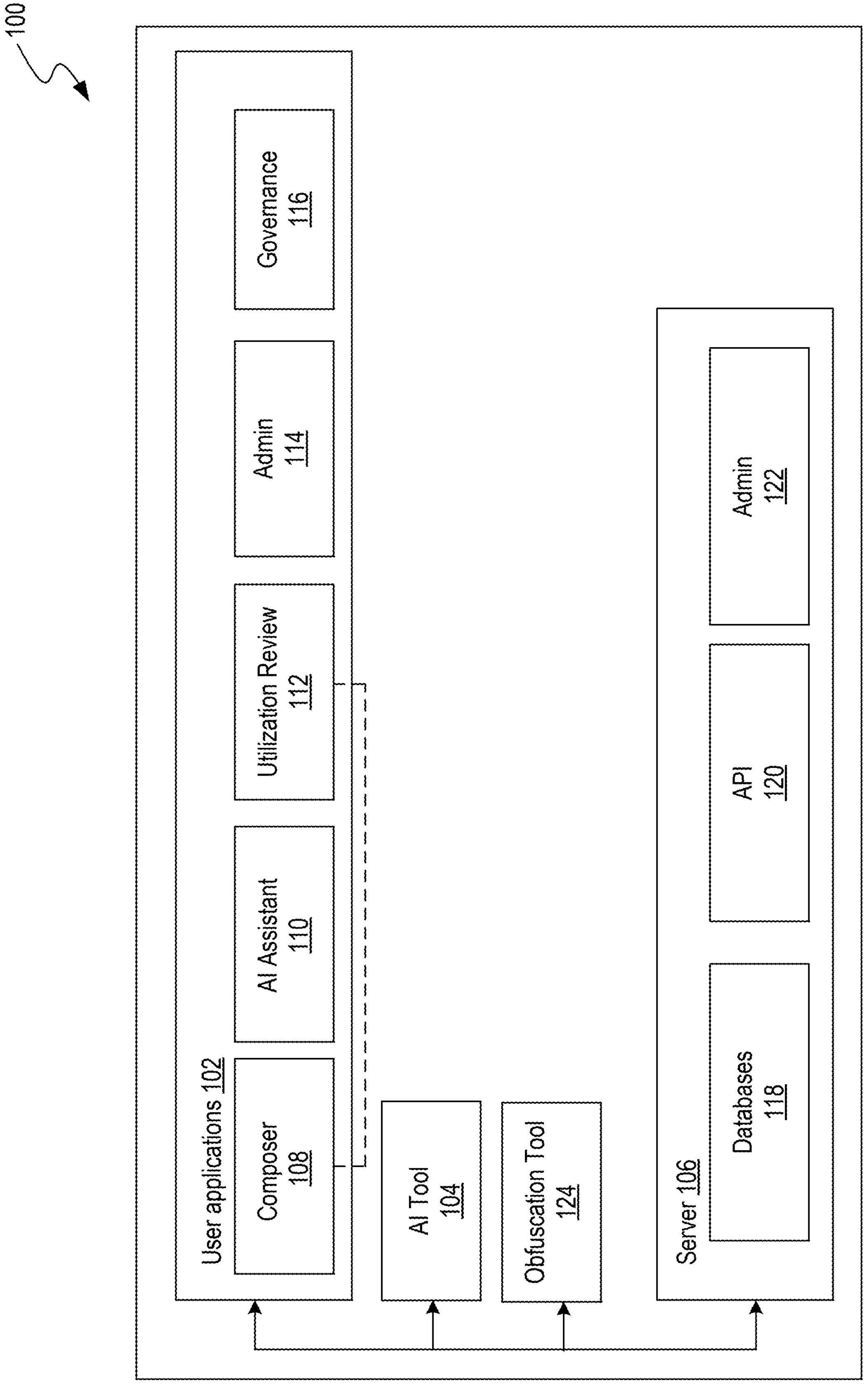
FIG. 1 illustrates a block diagram of an example platform, in accordance with some implementations of the present technology.

The technologies described herein will become more apparent to those skilled in the art by studying the Detailed Description in conjunction with the drawings. Embodiments or implementations describing aspects of the invention are illustrated by way of example, and the same references can indicate similar elements. While the drawings depict various implementations for the purpose of illustration, those skilled in the art will recognize that alternative implementations can be employed without departing from the principles of the present technologies. Accordingly, while specific implementations are shown in the drawings, the technology is amenable to various modifications.

DETAILED DESCRIPTION

The present technology provides for artificial intelligence (AI) processes and systems for healthcare. AI models can enable advanced methods for collecting and analyzing data and generating content with increased accuracy and efficiency. In healthcare, AI tools can be used for analyzing vast amounts of medical data, including patient records, research papers, clinical trial results, and patient care guidelines and requirements, and for preparing content (e.g., diagnostic reports, medical records, or patient care instructions). However, applying AI tools in healthcare can be challenging due to the complexity and variability of medical data including sensitive patient information. Additionally, ensuring the appropriate and accurate use of AI in healthcare is significant for, for example, maintaining patient privacy and achieving regulatory compliance.

Conventional methods of managing lineage and inspection for AI-generated artifacts often rely on manual documentation, version control systems, and basic logging frameworks to track changes and record metadata about models and data. Such conventional methods can lack the automation and integration needed to manage the complexity and scale of modern AI workflows effectively thereby causing inspection to be labor-intensive and time-consuming.

On one hand, manual lineage management and inspection (e.g., using human review) can be labor-intensive, inaccurate, and costly. For example, in an instance where an AI model is continuously updated with new data, manually documenting each change in data sources, preprocessing steps, and model parameters can become overwhelming and error prone. This can lead to incomplete or outdated records and therefore unattainable tracing of an exact lineage of the model and predicting the impact of each change on the model's performance. Manual documentation can also significantly increase the cost of generating and managing AI-generated artifacts. On the other hand, adding automation to lineage management and inspection can reduce the transparency and traceability of the AI model operations to the extent that inaccuracies and errors cannot be detected. For example, conventional methods using automated lineage management (e.g., Version Control Systems (VCS)) can track changes in code and configurations but they fall short in capturing the dynamic aspects of AI processes (e.g., data transformations and model training processes). In an instance where a data preprocessing script is modified, the automated management may not automatically track how this change affects the downstream models and their outputs, leading to gaps in the lineage information and challenges in reproducing results. Tracing any sources of errors and inspecting the generated artifacts becomes impossible with the lack of transparency of conventional automated management processes.

The present technology provides systems and methods for providing AI tools for healthcare with a hybrid lineage management and inspection that combines manual and automated approaches. Specifically, the present technology provides methods for automatically generating operation sets (e.g., workflows) for generating electronic artifacts for healthcare, methods for generating such artifacts with the operations sets, and an AI assistant for healthcare that all incorporate an automatically generated inspection feature. The inspection feature can enable a user to visually review, for example, the source data, the AI models and/or AI instructions used for generating the artifacts efficiently. The inspection feature can include, for example, displaying portions of source data used for generating the artifact concurrently with the artifact. The inspection feature thus allows for a level of user control over the generated artifacts without compromising efficiency.

Specifically, the present technology provides systems and methods for managing lineage and inspection of artifacts generated using AI models for healthcare with increased transparency and traceability using the inspection feature. The operations sets can be directed to generating content (e.g., healthcare-related artifacts such as utilization reviews), collecting, compiling, and analyzing data, and/or making decisions. Conventionally, generating operations sets for specialized needs, in particular those associated with complex data and requiring accuracy and compliance with regulations, can be time and resource-consuming, require specialized skills (e.g., skills of a software engineer and a healthcare professional), and have increased risk of inaccuracies and errors that are difficult to detect and track. In particular, adding automation, including the use of AI models, can reduce the transparency and traceability of the operations sets to the extent that inaccuracies and errors cannot be detected.

The technology can be facilitated by a user-friendly graphical user interface (GUI) (also referred to as "user interface") providing a guided process to create an operations set. This can reduce the need for specialized skills as well as decrease the time and resources consumed for operations set creation. The operations set processes can include processes for generating electronic artifacts using healthcare data sources and predefined AI agents. AI agents can include predefined AI models configured to generate electronic artifacts of particular types. The systems and methods can also include built-in mechanisms that enable transparency in reviewing the generated operations set processes and electronic artifacts generated using the operations set processes for accuracy and compliance with regulations and guidelines, thereby increasing transparency and audibility of the process of generating healthcare-related artifacts. The present technology can provide for operations sets that can provide more accurate artifacts, analyses, and decision-making.

For example, operations for managing lineage of artifacts generated using artificial intelligence (AI) models includes displaying a graphical user interface including multiple interface elements for receiving input. The graphical user interface is for generating an ordered operation in an operations set for generating an electronic artifact. The operations include receiving a first input on a first interface element of the multiple interface elements to provide a data source, wherein the data source is associated with medical data. It also involves receiving a second input on a second interface element of the multiple interface elements to select a particular AI agent from a set of AI agents, wherein the particular AI agent is associated with a particular AI model configured to generate an electronic artifact of a particular type associated with the medical data. Additionally, the operations include receiving a third input on a third interface element of the multiple interface elements to select a particular AI model from a set of AI models. Furthermore, the operations include receiving a fourth input on a fourth interface element of the multiple interface elements to provide a set of instructions for generating the electronic artifact. The operations include generating the ordered operation for the operations set for generating the electronic artifact. The operations set is configured to input the medical data from the data source and the set of instructions to the particular AI model agent, and cause an AI system to generate, using the particular AI agent with the particular AI model, the electronic artifact using the data source and the set of instructions. The generated ordered operation for the operations set enables lineage management for creating the electronic artifact in a manner that increases the transparency and traceability of the operations set, thereby decreasing inaccuracies and errors in the AI-generated artifacts.

The present technology also provides processes and systems for reviewing healthcare artifacts generated using AI (e.g., by the operations set processes described above) to, for example, inspect the accuracy of the artifacts. As explained above, a lack of transparency and traceability in AI operations sets can lead to inaccuracies and errors that are difficult to detect. The technology includes a GUI for displaying an AI-generated electronic artifact that is created using, for example, patient medical data and a set of instructions (e.g., a prompt). The patient medical data can be from a data source that is indicated in the set of instructions. The electronic artifact can include a medical status (e.g., including a diagnosis) and a confidence evaluation indicating the accuracy or quality of the medical status, as well as compliance with healthcare regulations. Further, the GUI can provide the inspection feature including the specific medical data used by the AI system to create the electronic artifact and source and/or content of specific healthcare regulations relevant for the specific medical data, thereby allowing the user to inspect the artifact's accuracy efficiently. As an example, the AI-generated artifact can include medical data having a description of the subject's symptoms, medical status (e.g., including a diagnosis for a condition), provided treatment, and any future care instructions. The AI-generated artifact can provide a utilization review including information about the medical data as well as an AI-generated assessment (e.g., a confidence level) for the accuracy of the diagnosis, the treatment and/or the care instructions. The assessment is generated by the AI using source artifacts, such as guidelines or standards associated with the medical data (e.g., guidelines or standards related to the treatment of the diagnosed condition). The inspection feature can provide portions (e.g., excerpts) of the source artifacts that are used by the AI in generating the assessment. This inspection feature can increase the transparency in the process of generating utilization reviews by the AI by increasing a (human) user's ability to review the AI-generated utilization review concurrently with sections of the source artifacts used to generate the utilization review.

For example, operations for providing artifact inspection using an artificial intelligence (AI) model includes displaying, on a first portion of a graphical user interface, an AI-generated electronic artifact. The AI-generated electronic artifact is created by an AI system using an input comprising medical data associated with a subject from a data source and a set of instructions. The AI-generated electronic artifact indicates a medical status for the subject created using the medical data, and the medical status identifies a user condition for the subject (e.g., user condition for a subject including a medical or health condition for a subject). The operations also include displaying, on a second portion of a graphical user interface, a confidence evaluation. The confidence evaluation comprises a numerical value, generated by the AI system using the medical data associated with the subject and historical medical status data, related to the accuracy or quality of the medical status or treatment of the subject. Responsive to an input on an interface element associated with the medical condition on the first portion of the graphical user interface, the operations include displaying, on a third portion of the graphical user interface, a portion of the medical data that the AI system used for the AI-generated electronic artifact. Displaying the AI-generated electronic artifact and the portion of the medical data enables a user to inspect the accuracy of the AI-generated electronic artifact.

The present technology further provides processes and systems for providing an AI assistant for healthcare applications. An AI assistant refers to an AI-powered software application designed to simulate human conversation and interact with users through text or voice interfaces. An AI assistant in healthcare can be used for generating answers to healthcare questions, providing decisions (e.g., diagnosis), evaluating compliance and effectiveness of care, evaluating the cost of care, etc. A choice of AI model (e.g., a language model) is a factor that affects the accuracy, efficiency, and cost of using AI assistants. In an industry where an AI assistant is used for analyzing and generating complex data while requiring a high level of accuracy and traceability, the choice of a language model is significant. However, current AI assistant technologies do not allow for the evaluation and selection of a language model but are generally directed to using a pre-defined language model. The present technology provides for a healthcare-related AI assistant that includes an evaluation of an appropriate language model to be used for specific types of tasks (e.g., based on cost, efficiency, latency, and document size) and further, includes the inspection feature that allows a user an ability to efficiently review the accuracy of the model.

For example, operations for providing an artificial intelligence (AI) assistant application include receiving, on an interface element on an AI assistant user interface, an input including a set of instructions to generate content by an AI system. The operations include determining, based on the set of instructions, a particular type of content the set of instructions is configured to generate. It includes generating, based on the set of instructions and the particular type of content, a prediction for an AI model for generating the content by the AI system. The prediction for the AI model indicates a particular AI model of a set of pre-defined AI models. Each of the set of pre-defined AI models has been evaluated for multiple types of content, the multiple types of content comprising the particular type of content. The evaluation is performed using historical AI-generated content generated by the set of pre-defined AI models. The method also includes receiving, on the AI assistant user interface, an input selecting the particular AI model. It involves transmitting to the AI system the set of instructions and an indication of the particular AI model. The AI system is configured to generate the content using the particular AI model and the set of instructions. Finally, the operations include displaying the generated content on the AI assistant user interface.

The description and associated drawings are illustrative examples and are not to be construed as limiting. This disclosure provides certain details for a thorough understanding and enabling description of these examples. One skilled in the relevant technology will understand, however, that the invention can be practiced without many of these details. Likewise, one skilled in the relevant technology will understand that the invention can include well-known structures or features that are not shown or described in detail, to avoid unnecessarily obscuring the descriptions of examples.

FIG. 1 illustrates a block diagram of an example platform 100. The platform 100 provides users with an all-in-one AI-integrated tool for healthcare. The platform 100 can include user applications 102, an AI tool 104, an obfuscation tool 124, and a server 106. The user applications 102, the AI tool 104, the obfuscation tool 124, and the server 106 are in communication with each other via a network.

In some implementations, the user applications 102 are cross-platform software applications configured to work on several computing platforms and web browsers. The user applications 102 can include a variety of applications directed to a variety of functions. Exemplary applications include a composer application 108, an AI assistant application 110, a utilization review application 112, an administration (admin) application 114, and a governance application 116. The user applications 108 through 116 can be all part of a multifunctional application that can be, for example, accessed through a common user interface. Alternatively, the user applications 108 through 116 can be separate applications in communication with each other.

The composer application 108 can be configured to create, manage, and deploy automated operations sets (e.g., workflows) for healthcare. The operations sets can be associated with, for example, collecting, compiling, and analyzing information from various data sources and generating artifacts based on such data sources. Artifacts (e.g., electronic artifacts) can include documents, written materials, images, video, audio, tables, charts, metadata, emails, messages, etc. The composer application 108 can specifically be used for generating processes with multiple tasks into an operations set with integrated AI. The composer application 108 can be used for generating user applications, or particular features or portions of such user applications, such as those user applications included in the user applications 102. For example, the utilization review application 112 can be generated and/or modified by the composer application 108. The AI assistant application 110 can be configured to simulate human conversation through natural language interactions. The AI assistant application 110 can generate content based on received instructions (e.g., prompts) and data sources (e.g., databases 118). Generating content can include answering questions, providing information, and performing tasks (e.g., summarizing or analyzing information). As an example, a user can provide the AI assistant application 110 a natural language question. In response to receiving the question, the AI assistant application 110 provides an answer that has been generated by an AI system using data sources available to the AI system. The utilization review application 112 can be configured to facilitate the evaluation of medical services and subject (e.g., patient) care. A utilization review is a process used by healthcare providers and insurers to evaluate the necessity, appropriateness, and efficiency of medical services and treatments to ensure optimal care and cost-effectiveness. The utilization review application 112 provides such an evaluation facilitated by assistance from an AI system. The admin application 114 can be configured to enable practical management and coordination of operations in healthcare organizations. Such operations can include, for example, managing staffing, budgeting, policy implementation, resources, training, and recordation. The governance application 116 can be configured to allow healthcare organizations to manage the compliance and accountability of their operations. The governance application 116 can be used to ensure that policies, procedures, and standards that guide the operation of the healthcare organizations are followed.

The AI tool 104 is an integrated software tool that enables AI-based functions for the user applications 102. In one example, the AI tool 104 is based on a neural network architecture, such as a transformer described with respect to FIG. 13. The AI tool 104 can be implemented on an AI system (e.g., an AI system described with respect to FIG. 12). The obfuscation tool 124 is an integrated software tool for real-time sensitive information protection. The obfuscation tool 124 can enable processes to conceal data processing logic and user inputs to reduce the risk of unauthorized access or data breaches. The operation of the obfuscation tool 124 is described in detail with respect to FIGS. 11A-11E.

The server 106 can include various units (e.g., compute and storage units) that enable the operations of the AI tool 104 and the user applications 102. The server 106 can include databases 118 (or data storages), an application programming interface (API) 120, and an administration (admin) unit 122. The databases 118 are configured to store data associated with the user applications 102. The data associated with the user applications 102 can include information about the content, the function, and/or any other information related to the user applications. The API 120 can be configured to communicate the data between the user applications 102, the AI tool 104, and the databases 118. The API 120 can also be configured to communicate with remote server systems, such as remote AI systems. For example, when a user performs a transaction within a user application, the API 120 processes the transaction and saves the changes associated with the transaction to the database 118. The server 106 can be in communication with external systems and software platforms. Such external systems and platforms can include other databases (e.g., cloud storage spaces), messaging software applications, or audio or video conference applications. The administration unit 122 is configured to manage and maintain the operations and tasks of the server 106. For example, the administration unit 122 can manage user accounts, data storage, security, performance monitoring, etc.

FIGS. 2 through 7 illustrate user interfaces for AI-based applications for healthcare, in accordance with some implementations of the present technology. Specifically, FIGS. 2 through 7 illustrate user interfaces associated with the user applications 102 of the platform 100 described with respect to FIG. 1.

Figure 2:
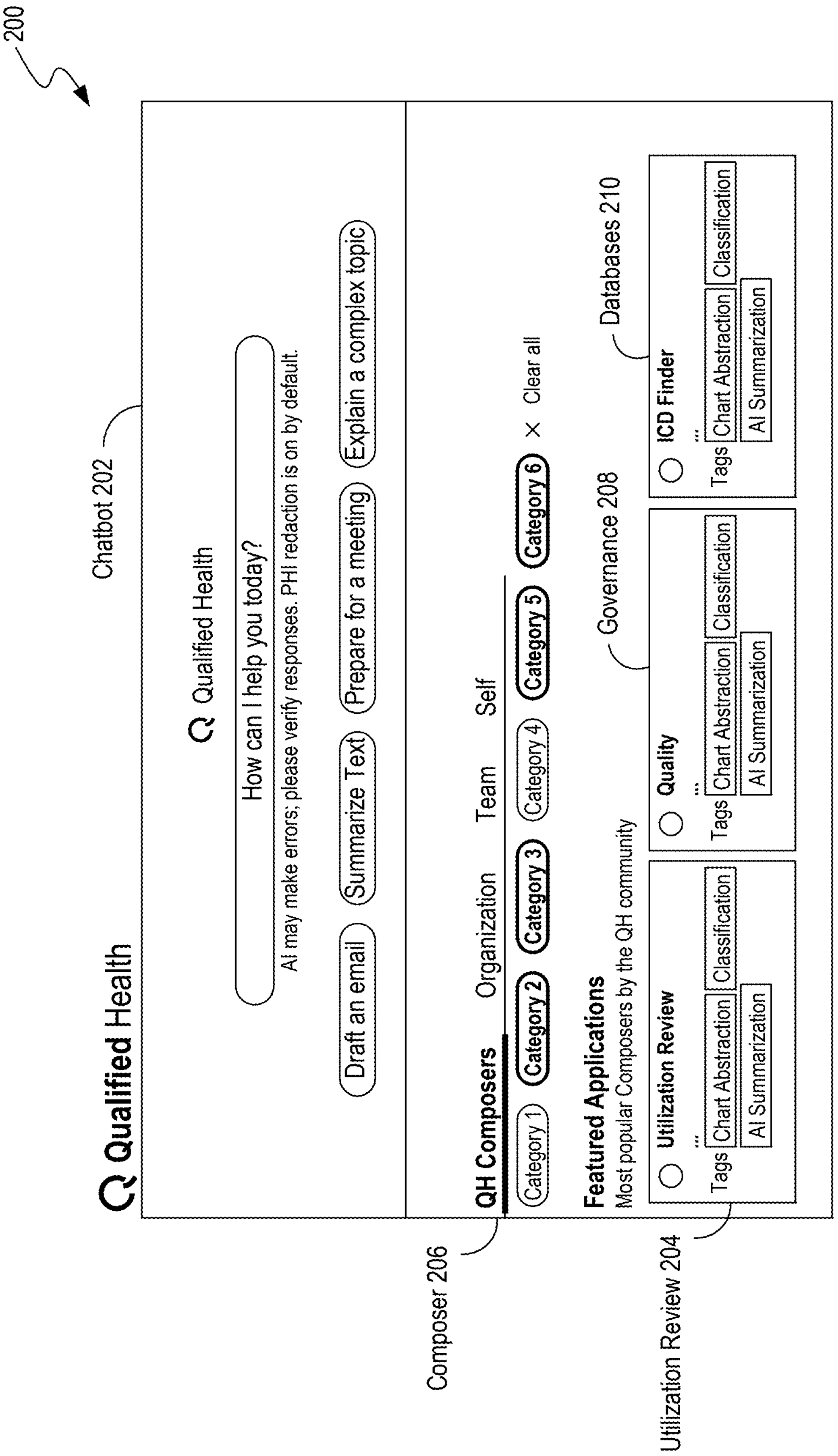
FIGS. 2 through 7 illustrate user interfaces for artificial intelligence (AI)-based applications for healthcare, in accordance with some implementations of the present technology.

FIG. 2 illustrates a main page 200 (e.g., a main user interface) associated with the platform 100. The main page 200 can serve as a central hub of the platform 100 providing users with an overview of key features and available applications associated with the platform 100. The main page 200 can include interface elements that allow a user to access the user applications 102. An interface element is an interactive component of a user interface (e.g., a button, icon, menu, or text box) that allows users to interact with and control a software application or system. An interface element is associated with a specific function, and a user input on the interface element causes the user interface to perform that specific function. As shown, the main page 200 includes interface elements associated with the AI assistant application 110 (e.g., AI assistant interface elements 202), the composer application 108 (e.g., composer interface elements 206), the utilization review application 112 (e.g., utilization review interface elements 204), and the governance application 116 (e.g., governance interface elements 208). Further, the main page 200 can include interface elements (e.g., databases interface elements 210) for accessing and performing searches on databases.

Figure 3A:
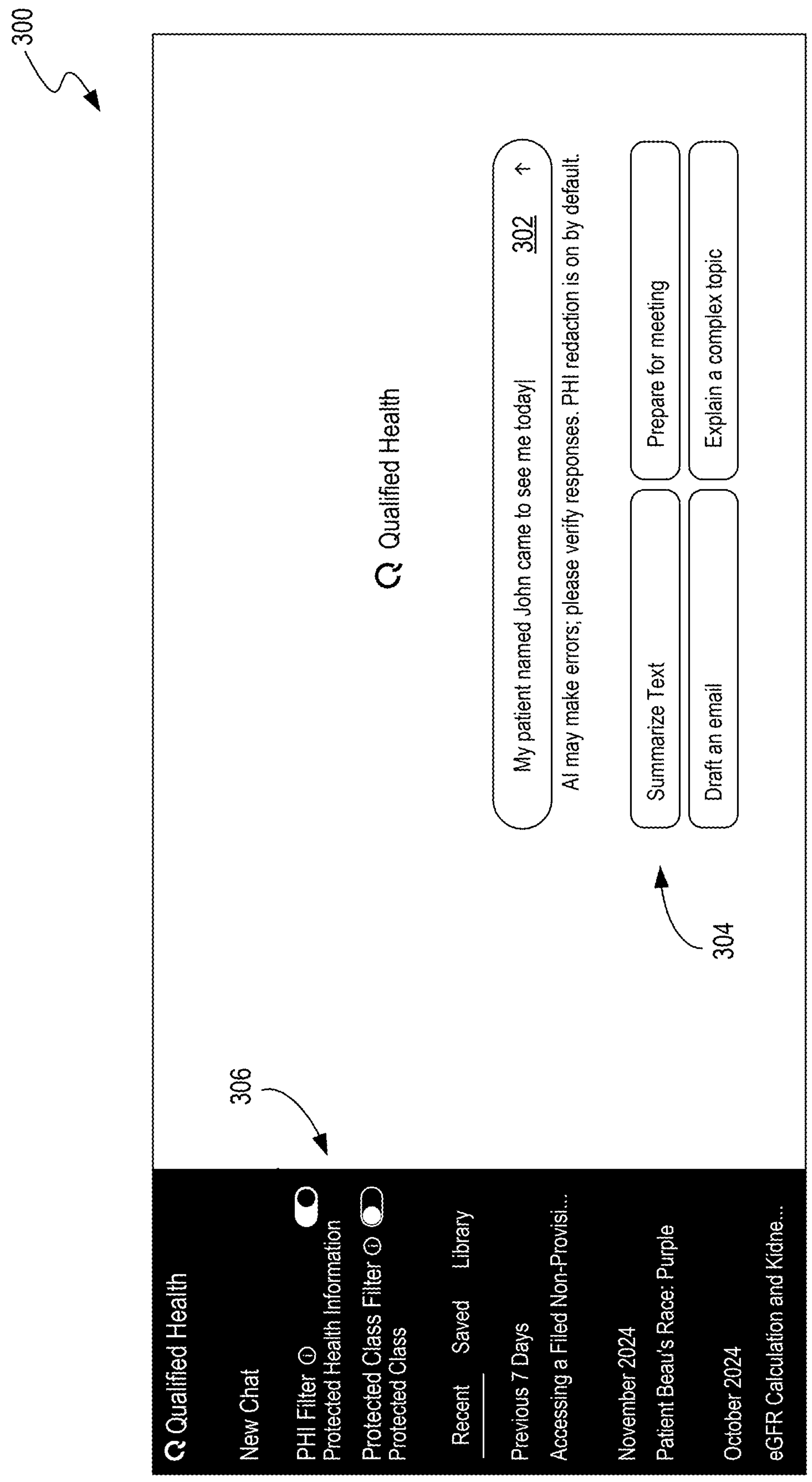
Figure 3B:
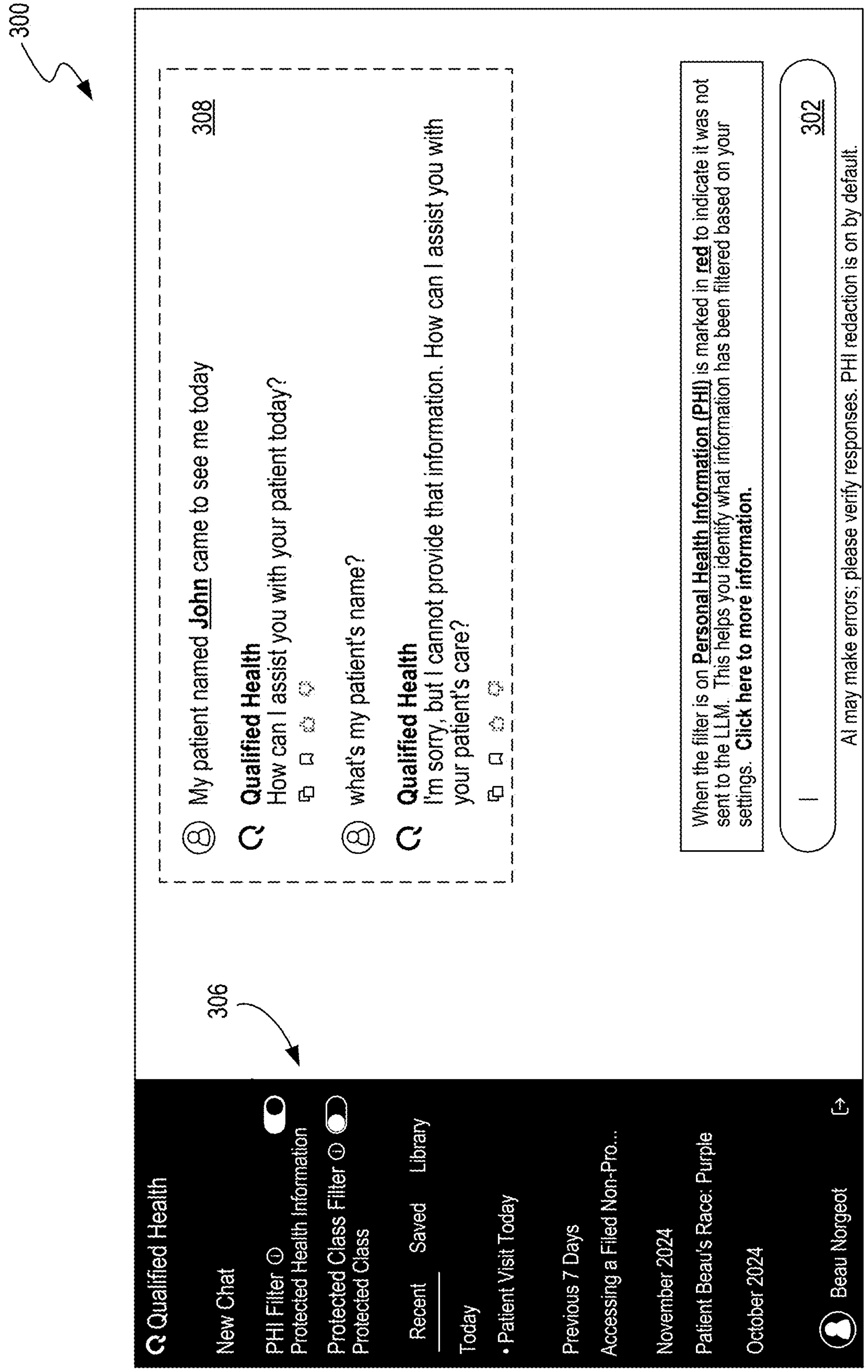

FIGS. 3A and 3B illustrate an AI assistant user interface 300 associated with the AI assistant application 110 described with respect to FIG. 1. The AI assistant user interface 300 includes a text input interface element 302 configured to receive an input (e.g., a natural language input, also referred to as a "prompt") from a user. The input can include a set of instructions in a form of natural language. For example, in FIG. 3A, a user has provided the text "My patient named John came to see me today" to the text input interface element 302 (e.g., the user is interested in receiving information related to the patient named John). The user can also select an input from predefined natural language prompts 304 provided on the AI assistant user interface 300 (e.g., for summarizing text, drafting an email, preparing for a meeting, or requesting an explanation for a complex topic). A prompt provided by a user is configured to be communicated to and processed by the AI tool 104 described with respect to FIG. 1. The prompt is transmitted by the AI tool 104 to an AI system (e.g., as described in FIG. 12). The AI system processes the prompt using a language model and generates content in response to the prompt.

The AI assistant user interface 300 can also allow a user to choose a filter 306 that restricts information that is being sent to the AI system, e.g., by a process of obfuscation. The filtering can be performed, for example, by obfuscation methods and systems described in U.S. Provisional Application No. 63/735,162, titled "System and Method for Real-Time Obfuscation and De-obfuscation of Sensitive Information in Large Language Model Communications," filed Dec. 17, 2024, which is incorporated herein. The filtering can be applied when handling sensitive information to deliberately make the data impossible to understand or interpret by unauthorized users, thereby protecting it from being easily accessed, read, or exploited while still allowing it to be processed or transmitted securely. Such filtering is especially important in healthcare applications that transmit subject information. The filters can include, for example, a filter for protected class information or protected health information (PHI). When a filter is applied, the AI system is restricted from receiving the information protected by a filter (e.g., a subject's name). For example, as shown in FIG. 3B, the subject name "John" is identified as protected health information and is therefore protected under the PHI filter. The AI system therefore has no information associated with the subject's name and thereby does not generate questions that would respond to a prompt that includes the subject's name. Instead, the content generated by the AI system, as illustrated in the chat portion 308 of the AI assistant user interface 300, includes a response "I'm sorry, but I cannot provide that information . . . ."

Figure 4B:
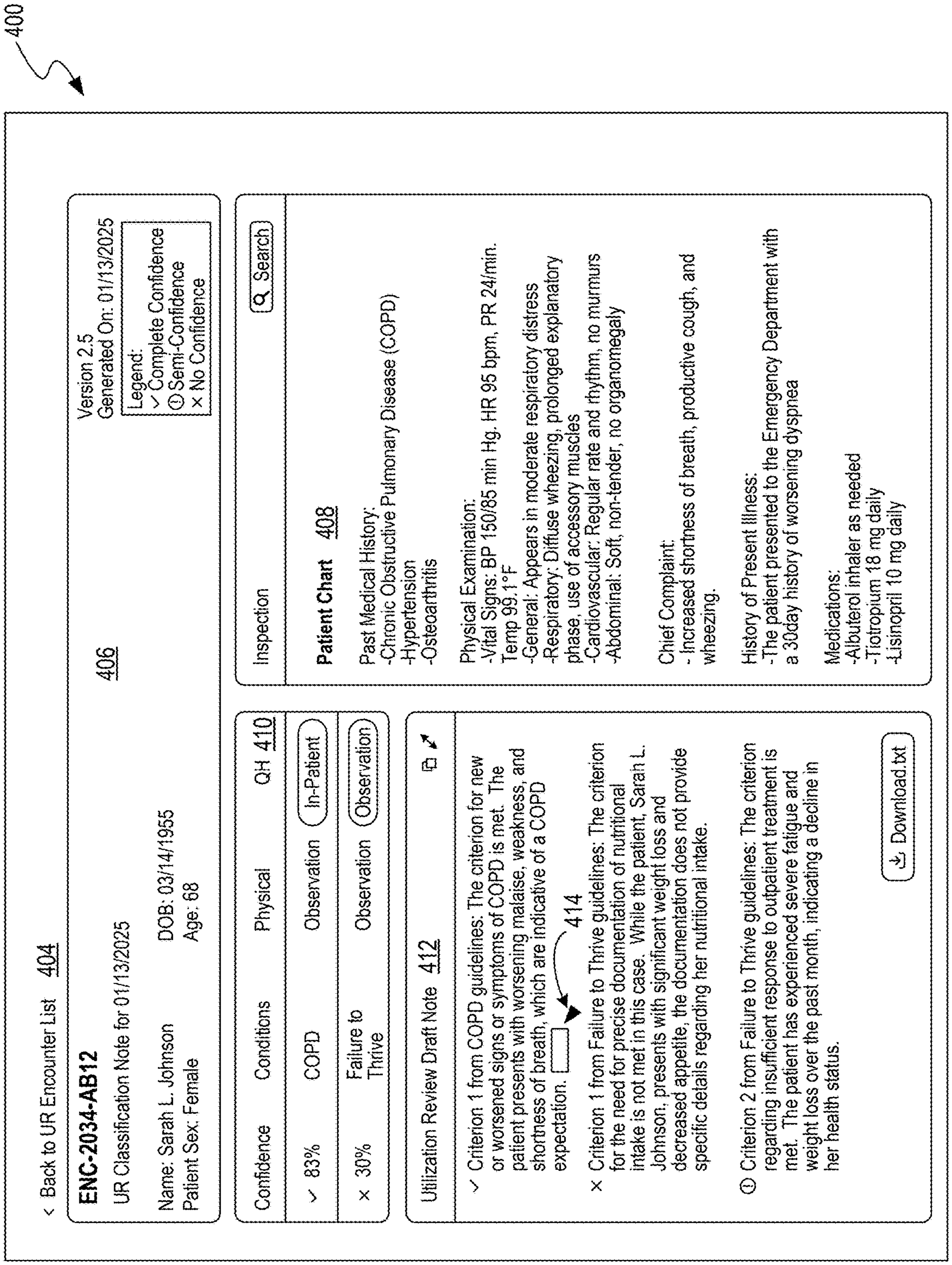

FIGS. 4A and 4B illustrate a utilization review user interface 400 associated with the utilization review application 112 described with respect to FIG. 1. FIG. 4A illustrates a table including multiple utilization reviews 402 associated with subjects. A utilization review can be an artifact (e.g., an electronic artifact) used for assessing the necessity, appropriateness, and efficiency of medical services and treatments provided by a healthcare provider to a subject. Utilization reviews can be useful for health insurance companies, healthcare providers, patients, government agencies, employers providing health benefits to employees, etc. Utilization reviews can be used to assess, for example, whether treatment and care of a subject was cost-effective, complied with regulations and standards, and was effective in treating the subject's condition. As an example, as part of evaluating whether a subject requires surgery, a health insurance company can conduct a prospective utilization review to determine whether the surgery is medically necessary or beneficial based on the subject's condition and medical history.

The utilization reviews 402 can include content generated by an AI system (e.g., the AI tool 104 in FIG. 1). The utilization reviews 402 can be produced by a utilization review operations set generated by the composer application 108 in FIG. 1. As shown, the table in FIG. 4A provides an identifier (ID) (e.g., an encounter ID associated with a subject and/or a particular incident of treatment of the subject), information regarding the subject (e.g., sex), insurance information, and a classification of whether the subject should be treated as an "in-patient" or "observation" subject provided by a physician and an AI system (e.g., "QH Classification"). The table further provides a confidence level assessment for the classification (e.g., in percentages). By providing an input to select one of the utilization reviews 402 in FIG. 4, a user can open an electronic version of the utilization review, as shown in FIG. 4B.

In FIG. 4B, the utilization review user interface 400 provides a utilization review artifact 404 associated with a particular encounter ID from the utilization reviews 402 in FIG. 4A. The utilization review 402 is an exemplary utilization review for a subject that has been diagnosed with two conditions (e.g., chronic obstructive pulmonary disease (COPD) and failure to thrive) and has been classified for "in-patient" care (COPD) and "observation" (failure to thrive). The utilization review is prepared for the purpose of evaluating whether the classification and medical status was accurate in light of guidelines and standards associated with these diagnoses. Utilization reviews can be prepared for other purposes as well, as described above.

The utilization review artifact 404 includes multiple sections including a subject information section 406, a confidence level section 410, a note section 412, and an inspection section 408. The subject information section 406 includes information associated with the subject (e.g., name, date of birth, age, sex, an encounter ID).

The note section 412 can include an AI-generated description and an assessment associated with the utilization review. For example, as shown, the note section 412 provides an AI-generated assessment of the medical status and whether each of the diagnoses is in compliance with guidelines for such medical status. The AI-generated evaluation can be done, for example, using an AI algorithm trained to analyze a subject's medical records against guidelines for a given condition, length of stay, intensity of service, and/or procedures performed. The AI-generated description and assessment can be done using the subject's medical record as well as guidelines and standards associated with medical status of the two conditions as an input. The AI tool 104 can access such input artifacts from the databases 118 in FIG. 1. As shown, the note section 412 indicates that the subject's medical status and classification related to the COPD is appropriate while the subject's medical status and/or classification for the failure to thrive was not appropriate. The confidence level section 410 further summarizes the utilization review results by the AI system by providing a confidence level (e.g., in percentage) for each of the diagnosed conditions.

Further, the inspection section 408 provides to a user an efficient and user-friendly manner of reviewing the utilization review results. In some implementations, the inspection section 408 is displayed in response to a user input on an interface element (e.g., an interface element 414) on the note section 412. In response to the input on the interface element 414, associated with the assessment related to the COPD diagnosis, the inspection section 408 displays a portion of a source artifact that the AI system has used to generate the assessment for the utilization review. For example, in FIG. 4B, the inspection section 408 displays a portion of a subject chart. The inspection section 408 can also display portions of other artifacts, such as guidelines and standards associated with the COPD. In some implementations, the specific portions of the source artifact can be highlighted (e.g., by a color, shading, or pattern) to indicate specific language that the AI system used for generating the utilization review. The inspection section 408 increases transparency in the process of generating utilization reviews by an AI system by increasing the user's (e.g., a human user's) ability to review the AI-generated review concurrently with sections of the source artifacts used to generate the review.

Figure 5A:
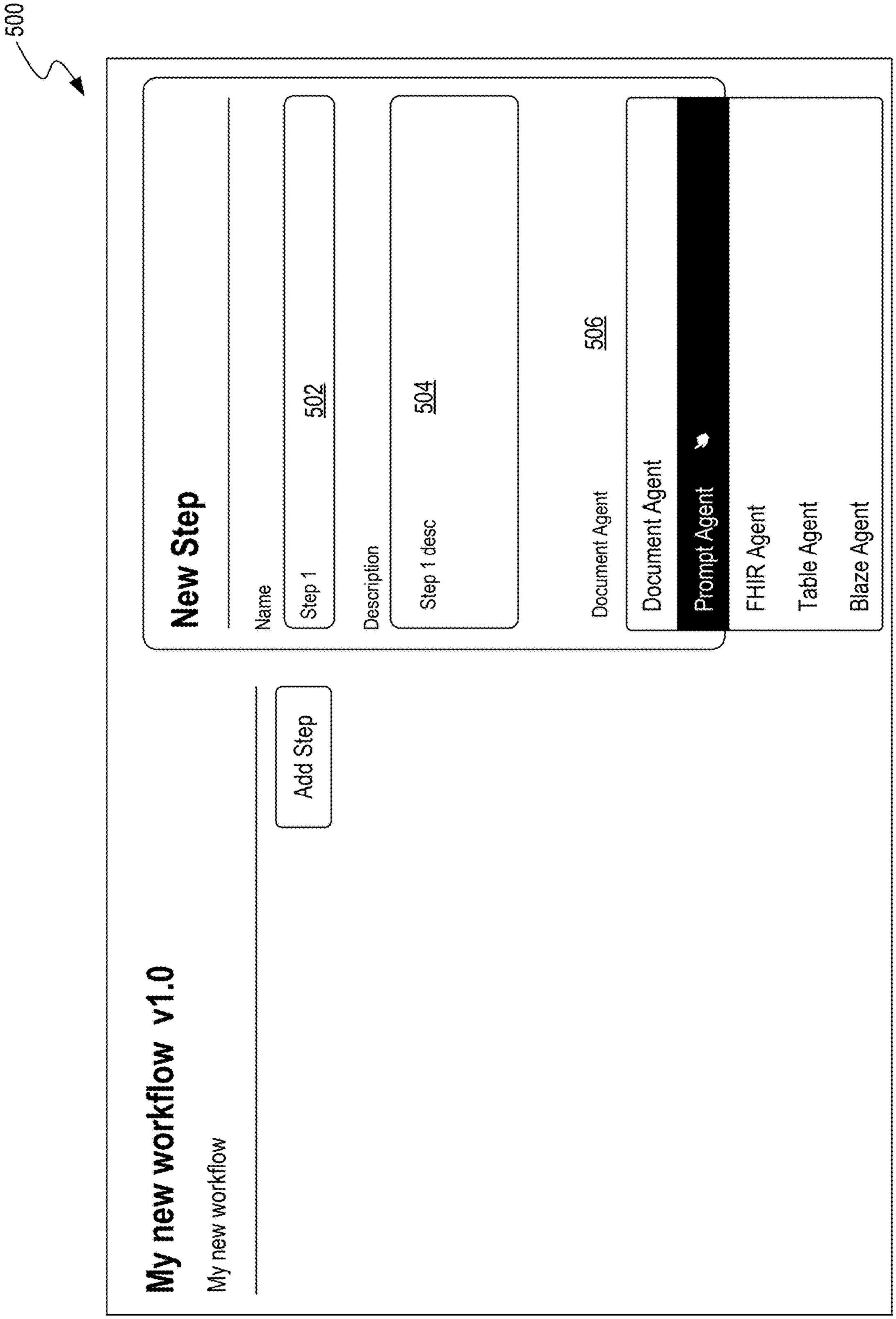
Figure 5B:
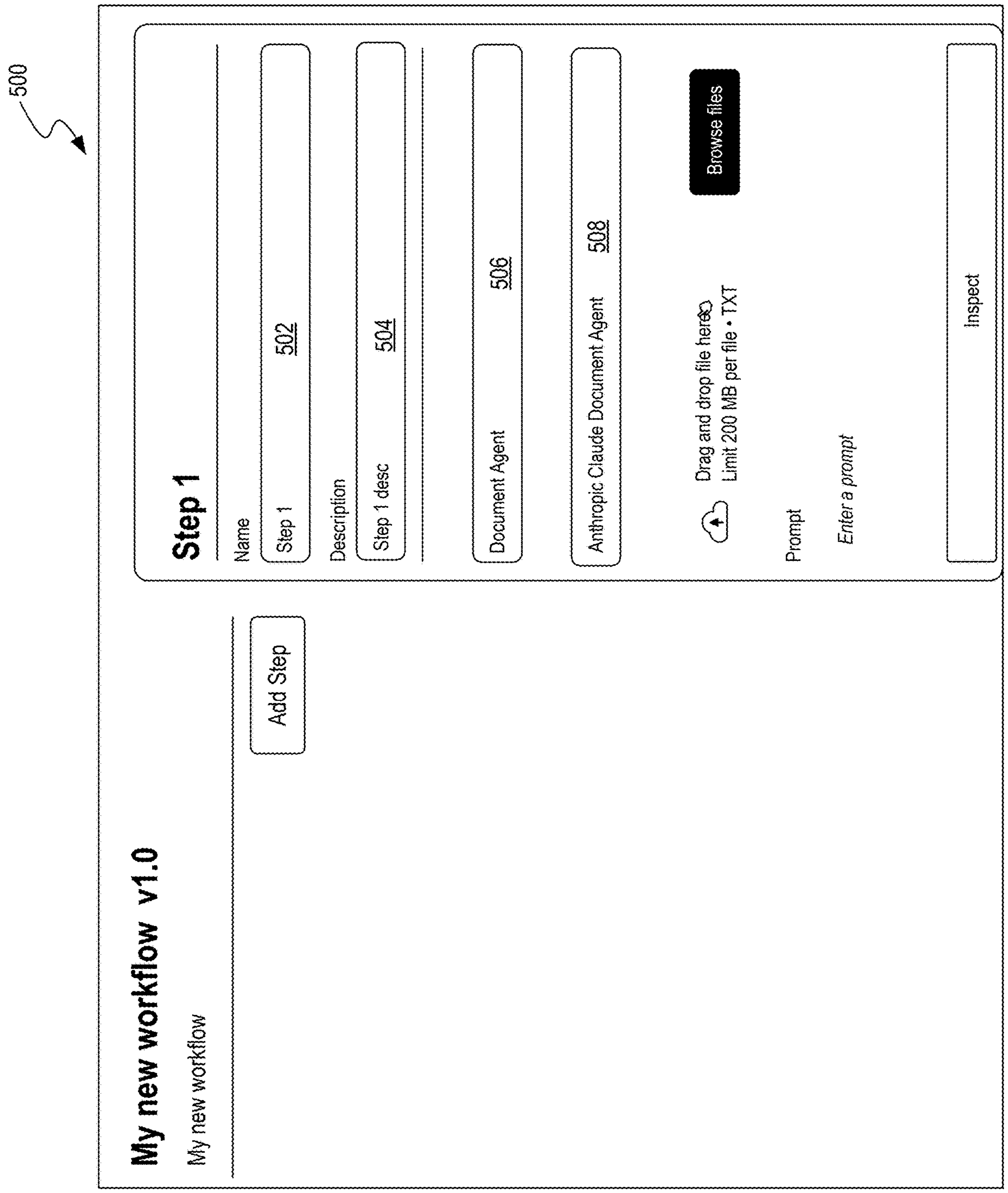
Figure 5C:
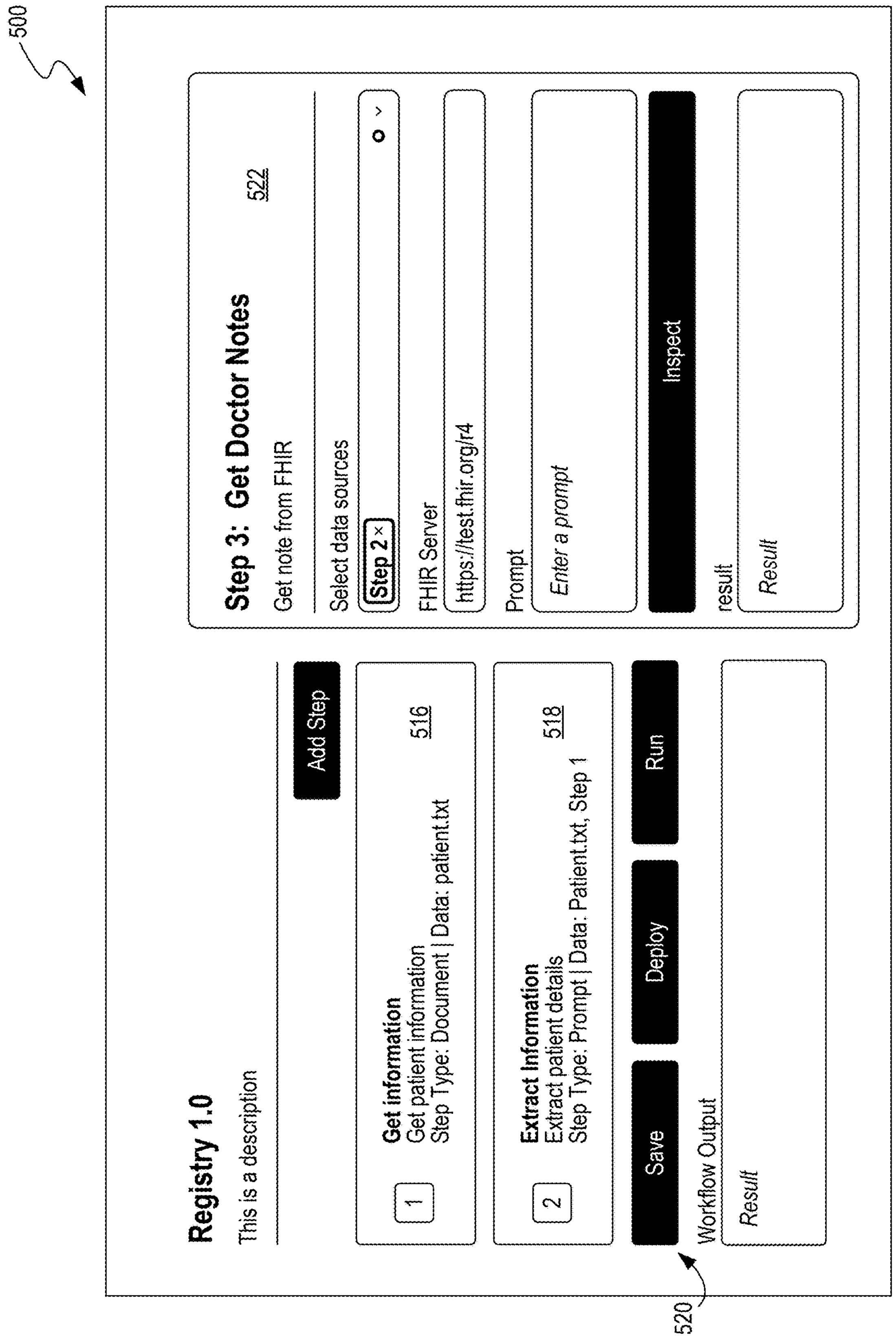

FIGS. 5A through 5C illustrate a composer user interface 500 associated with the composer application 108 described with respect to FIG. 1. As described with respect to FIG. 1, the composer application 108 can be configured to create, manage, and deploy automated operations sets for healthcare. The operations sets can be associated with, for example, collecting, compiling, and analyzing information from various data sources and generating artifacts based on such data sources. The composer application 108 is in communication with the AI tool 104 and can be used for generating operations sets with multiple ordered operations (e.g., also referred to as operations) involving AI. The composer user interface 500 is configured to guide a user to provide input for generating an operations set, in particular an operations set associated with generating electronic artifacts, performing analyses, compiling data, or any other operations sets associated with healthcare by integrated AI (e.g., the AI tool 104 in FIG. 1).

As shown in FIGS. 5A and 5B, the composer user interface 500 includes multiple interface elements configured to receive user input. The combination of the inputs can form an ordered operation in an operations set. Multiple ordered operations can be combined to form a multioperation operations set. An interface element 502 is configured to receive a name for the operation in the operations set process and an interface element 504 is configured to receive a description for the operation in the operations set process.

An interface element 506 is configured to receive a selection of an AI agent. An AI agent can include predefined instructions (algorithms) and features that are configured for performing certain AI-based tasks. The tasks can include generating content, analyzing content, collecting and compiling data, and/or making decisions. The AI agent can involve natural language processing. The AI agents available for selection include a table agent configured to generate an electronic artifact having a table format, an abstractor agent configured to extract and standardize structured content from a medical record or an unstructured artifact, an artifact agent configured to generate a medical record artifact associated with a subject, a prompt agent configured to generate a natural language response to a query, and a standard agent (e.g., a fast healthcare interoperability resources (FHIR) agent in FIG. 5A) configured to generate an electronic artifact complying with a healthcare information standard.

An interface element 508 is configured to receive a selection of a language model. Exemplary language models include GPT-4, Anthropic Claude, BERT (Bidirectional Encoder Representations from Transformers), T5 (Text-To-Text Transfer Transformer), RoBERTa (Robustly optimized BERT approach), XLNet, ALBERT (A Lite BERT), Turing-NLG, Megatron-LM, and ERNIE (Enhanced Representation through Knowledge Integration). An interface element 510 is configured to receive an input to select or provide source data. The source data can be selected from the databases 118 or from an additional source data. An interface element 512 is configured to receive a prompt for performing the operation of the operations set. A prompt includes a set of instructions (e.g., natural language instructions) to perform the task, using the selected AI agent and language model. An interface element 514 is configured to receive an input to inspect the operation of the operations set, as defined by the user inputs on the interface elements 502 through 512. The inspection can include, for example, providing an AI-generated evaluation of the defined operation of the operations set.

FIG. 5C illustrates a feature of combining multiple operations into an operations set. In FIG. 5C, an operations set includes operation 1 (operation 516, "Get Information") and operation 2 (operation 518, "Extract Information"). A further operation 3 in a section 522 is being added, as described with respect to FIGS. 5A and 5B. As shown, in the section 522, the data source is selected as operation 2, indicating that the outcome of the operation 518 is used as the input data source for operation 3. As shown in FIG. 5C, the operations set generated by the composer application 108 can be saved, deployed, and run by user input on the respective interface elements 520.

Figure 6A:
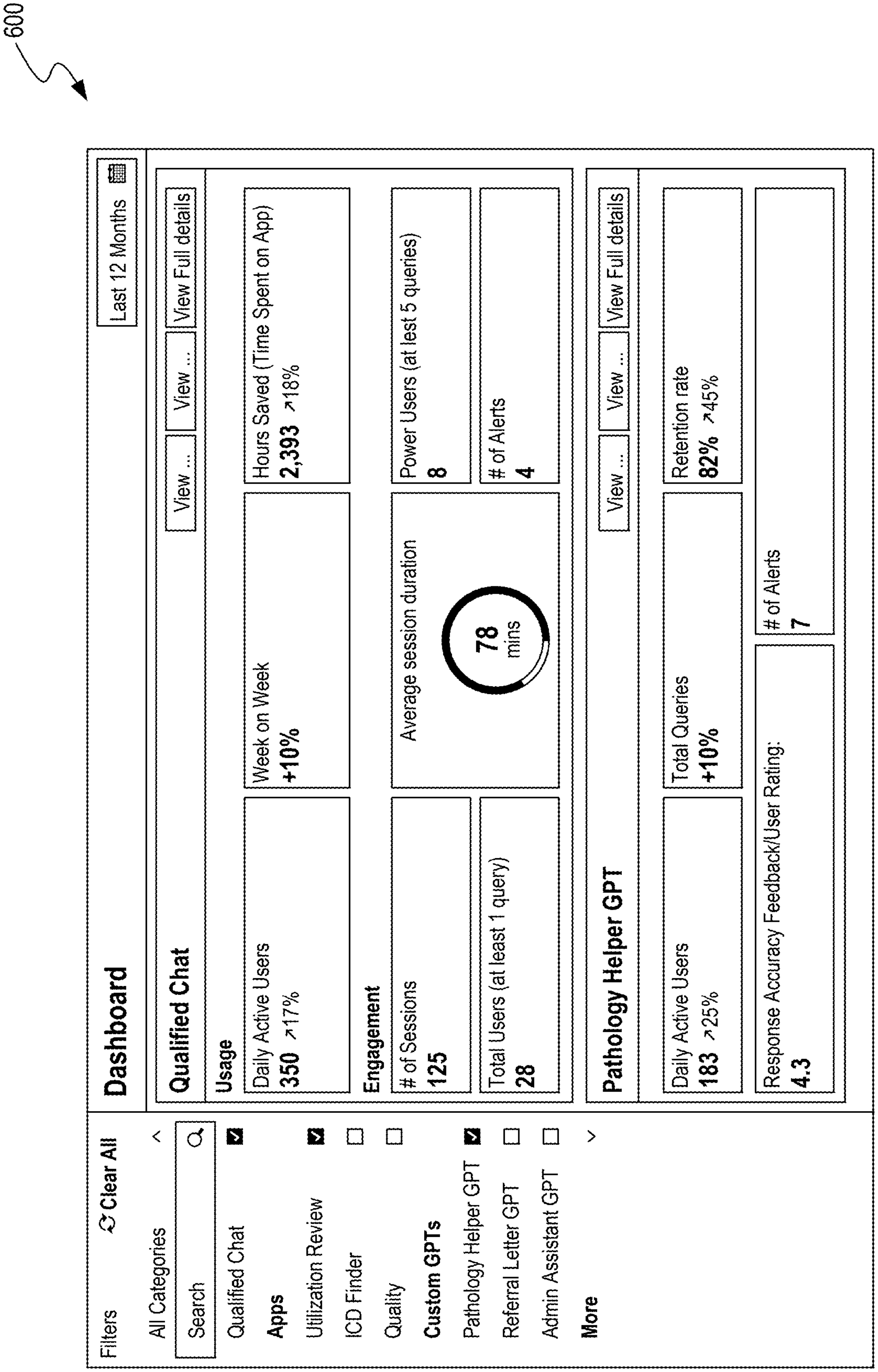
Figure 6B:
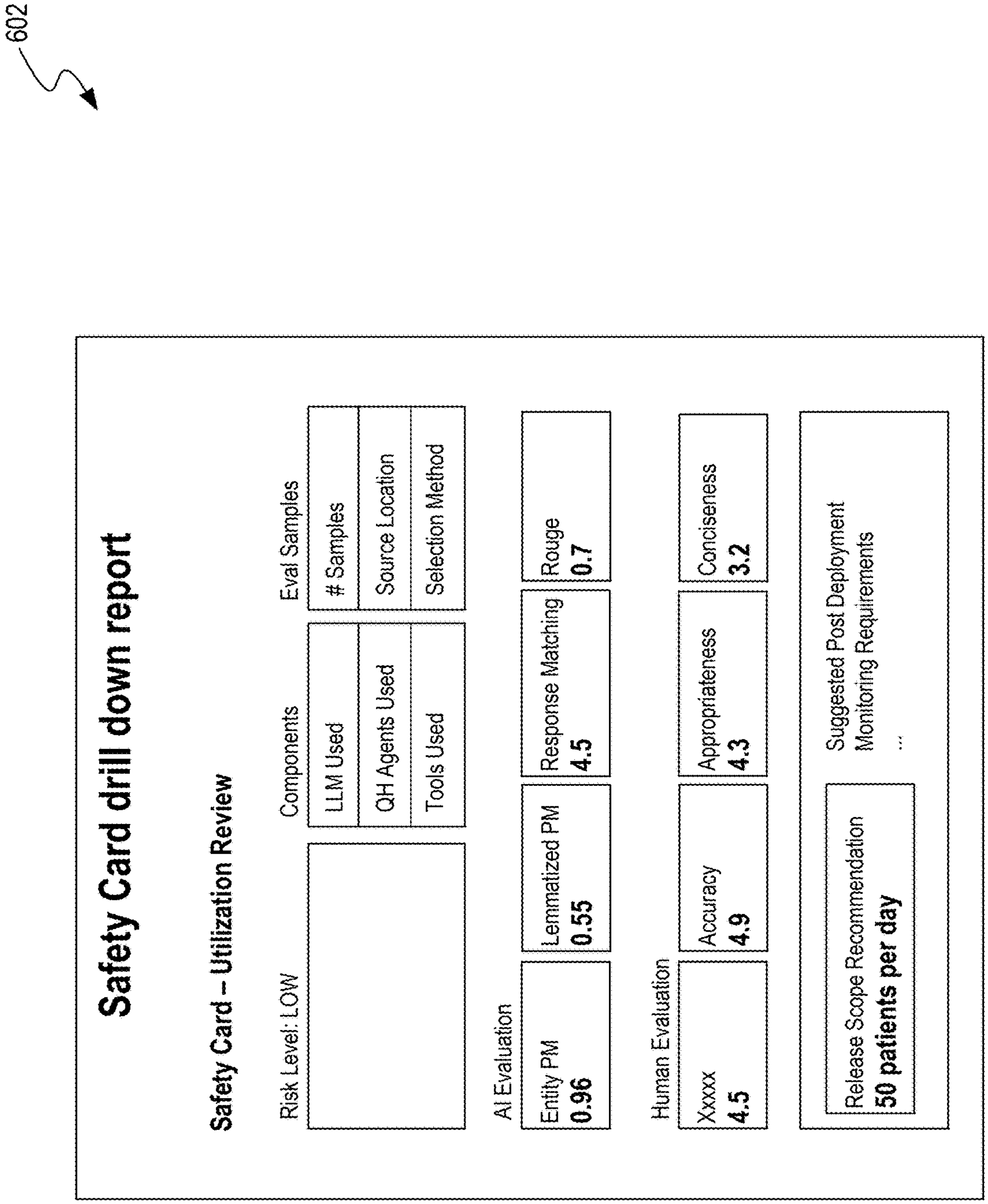
Figure 6C:
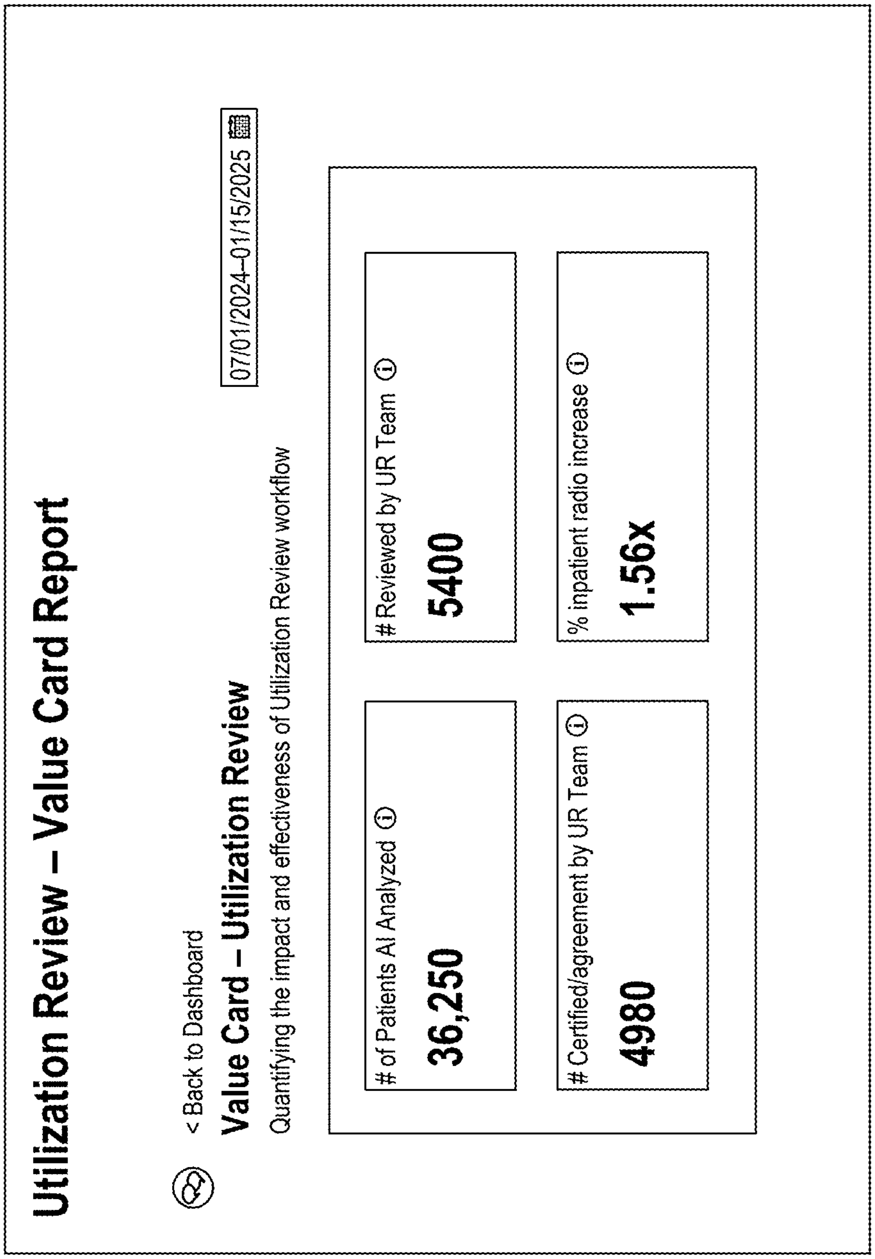

FIGS. 6A through 6C illustrate user interfaces associated with the admin application 114 described with respect to FIG. 1. These user interfaces can enable a user to review and control a variety of features of the platform 100. A user interface 600 in FIG. 6A includes a dashboard that can provide information related to usage and user engagement of different applications of the platform 100. A user interface 602 in FIG. 6B includes an exemplary data report generated by the system. The data report can be a type of utilization review, as explained with respect to FIGS. 4A and 4B. Here, the report is associated with a safety card drill down. Such a report can provide a detailed analysis on safety incidents recorded by a healthcare provider and can be used for identifying and addressing safety issues. As described with respect to, for example, the utilization review in FIG. 4B, a safety card drill down can include an AI-generated evaluation, a human-generated evaluation, and features that allow a user to inspect the analyses provided by the AI system (e.g., by reviewing source artifacts). A user interface 604 in FIG. 6C includes a type of utilization report that provides information on value provided by the applications of the platform 100. For example, the user interface 604 includes a comparison between a number of AI analyzed subject records (e.g., 36,250) versus a number of subject records reviewed by a team of professionals (e.g., 5400).

Figure 7:
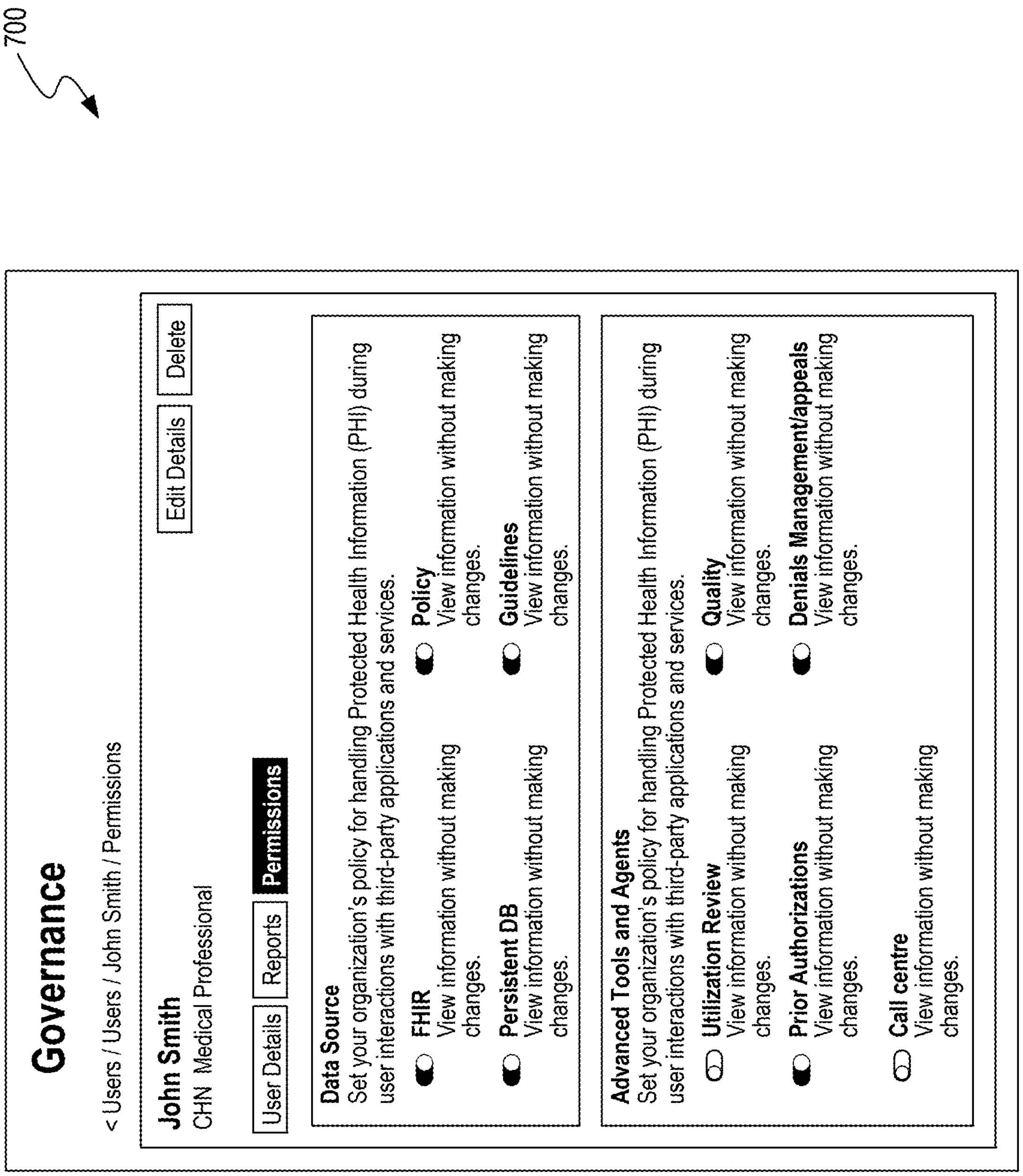

FIG. 7 illustrates a user interface 700 associated with the governance application 116. The governance application 116 can be configured to evaluate whether policies, procedures, and standards that guide the operation of the healthcare organizations are followed. As an example, the governance application 116 can be used to define, monitor, and manage authorizations for users within the organization.

Figure 8:
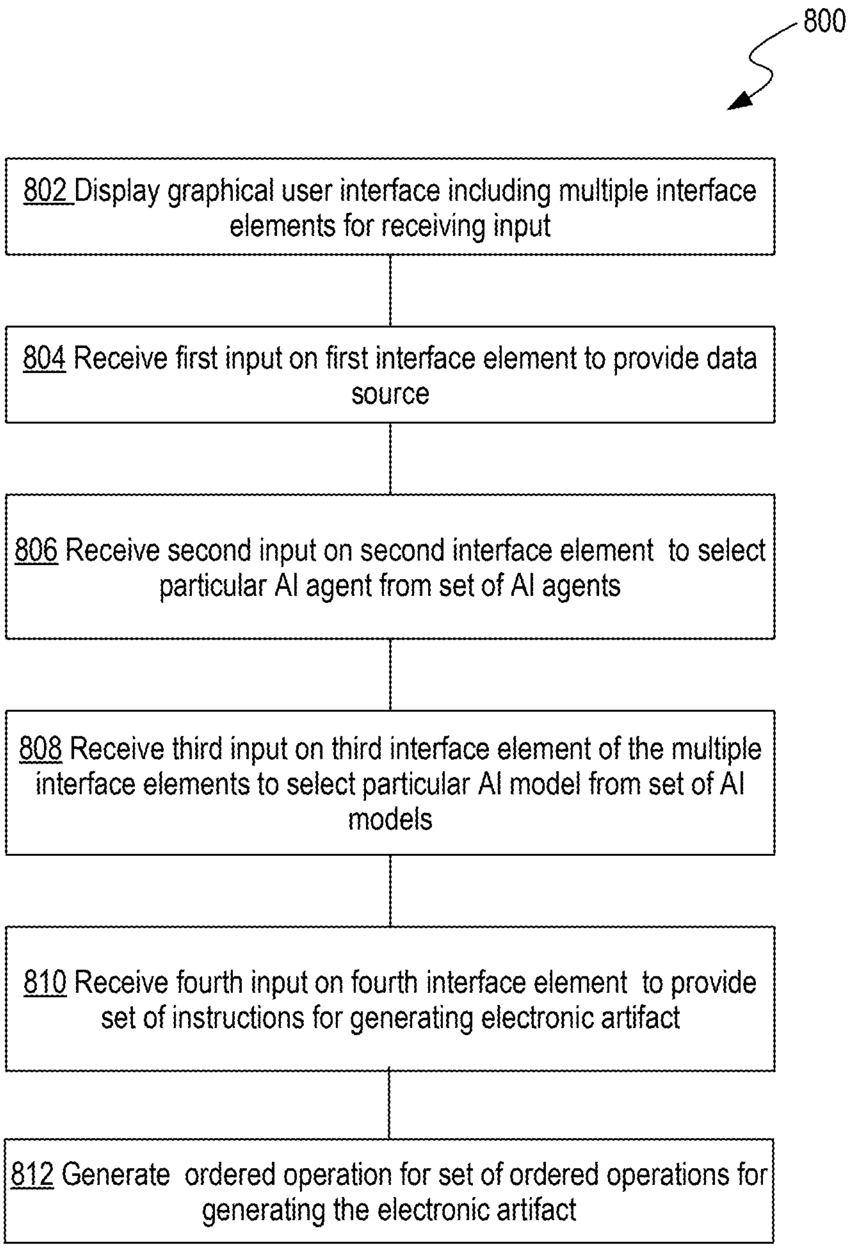
FIG. 8 is a flow diagram illustrating a process for managing lineage of artifacts generated using artificial intelligence (AI) models, in accordance with some implementations of the present technology.

FIG. 8 is a flow diagram illustrating a process 800 for managing lineage of artifacts generated using artificial intelligence (AI) models. The process 800 can be performed by a computing device or a system (e.g., a computer system 1400 described with respect to FIG. 14). The process 800 can include displaying a graphical user interface such as the user interfaces described with respect to FIGS. 5A-5C.

The process 800 is directed to a composer configured to generate AI-driven operations sets specifically for healthcare applications. These operations sets can be used for generating healthcare-related artifacts, collecting and analyzing data, and making decisions. Traditionally, creating such specialized operations sets is time-consuming, resource-intensive, and requires specialized skills from both software engineers and healthcare professionals. Additionally, there is a higher risk of undetected inaccuracies and errors, especially when automation and AI models are involved, which can further reduce transparency and traceability. The composer of process 800 can enable the creation, management, and deployment of complex healthcare operations set processes using an integrated AI tool, thereby reducing the need for specialized skills and resources. It includes processes for generating electronic artifacts from healthcare data sources using predefined AI models, ensuring accuracy and compliance with regulations. Built-in mechanisms enhance transparency and auditability, leading to more accurate artifacts, analyses, and decision-making. The operations created by the composer process 800 can be implemented as user applications, or as features or portions of user applications (e.g., such as the user applications 102 described with respect to FIG. 1). Once created, such user applications can operate independently from the composer process. The applications can also be modified and/or updated by the composed process. As an example, the utilization review application 112 in FIG. 1 (also described with respect to FIGS. 4A, 4B and 9) and can be created either partially or fully by the process 800.

At 802, the device can display a graphical user interface (e.g., user interface 500 in FIGS. 5A-5C) including multiple interface elements (e.g., interface elements 502-514) for receiving input. The graphical user interface can be for generating an ordered operation for an operations set for generating an electronic artifact using AI. Similarly, the graphical user interface can be configured to generate an ordered operation for other operations sets, such as making decisions, analyzing data, presenting data, etc. The operations sets can be used by a variety of healthcare entities and individuals, for example, insurance companies, healthcare providers, subjects, government agencies, employers providing health benefits to employees. As an example, a subject can be a patient such as an inpatient or an outpatient associated with a healthcare entity, or a client of a healthcare provider or an insurance company.

At 804, the device can receive a first input on a first interface element of the multiple interface elements to provide a data source (e.g., the interface element 510 in FIG. 5B). The data source can be associated with user data associated with one or more subjects. User data can include medical data, personal data or other health-related data associated with one or more subjects. For example, user data associated with a subject can include medical data of a patient of a healthcare facility or entity, or of a client of a healthcare provider or an insurance company. As used herein, a user can refer to a subject, such as a patient or a client associated with a healthcare-related entity or facility. Depending on the type and purpose of the operations set being generated by the composer, the data source can also be associated with other healthcare-related artifacts or databases. In some implementations, the medical data associated with one or more subjects includes text data, audio data, tabular data, image data, and/or video recording data.

At 806, the device can receive a second input on a second interface element (e.g., interface element 506 in FIG. 5B) of the multiple interface elements to select a particular AI agent from a set of AI agents. The particular AI agent can be configured to generate electronic artifacts of specific types using predefined AI models (e.g., language models) which can include pre-defined instructions or parameters The particular AI agent can be associated with a particular AI model configured to generate an electronic artifact of a particular type associated with medical care of the one or more subjects.

At 808, the device can receive a third input on a third interface element of the multiple interface elements to select a particular AI model (e.g., the interface element 508 in FIG. 5B) from a set of AI models.

At 810, the device can receive a fourth input on a fourth interface element (e.g., the interface element 512 in FIG. 5B) of the multiple interface elements to provide a set of instructions for generating the electronic artifact.

At 812, the device can generate the ordered operation for the operations set for generating the electronic artifact using AI. The generated ordered operation can be saved, run, or deployed, e.g., in response to user input on interface elements 520 in FIG. 5C. The operations set can be configured to input medical data associated with the one or more subjects from the data source and the set of instructions to the particular AI agent. The operations set can be configured to cause an AI system to generate, using the particular AI agent with the particular AI model, the electronic artifact using the data source, and the set of instructions. For example, the device transmits the information identified in the user interface, including the data source, the set of instructions, the particular AI agent, and an indication of the particular AI model to an AI system (e.g., the AI system described with respect to FIG. 12 that is configured to operate AI models (e.g., as described with respect to FIG. 13).

It is understood that any of the inputs for the data source, AI agent, AI model, the set of instructions can be optional and can be provided in a different order. Some of the inputs may be defined as default (e.g., without any further input, the device selects a certain AI model, data source, or AI agent).

In some implementations, the ordered operation for the operations set for generating the electronic artifact is a first ordered operation and the electronic artifact generated using the first ordered operation is a first electronic artifact. The device can further receive additional inputs to add a second ordered operation to the operations set for generating a second electronic artifact. The additional inputs can include an input for providing an additional data source, an input for selecting an additional AI agent from a set of AI agents, an input for selecting an additional AI model, and an input to provide an additional set of instructions. The additional data source can indicate the first electronic artifact generated by the first ordered operation. For example, as described with respect to FIG. 5C, an operations set can include multiple ordered operations (e.g., ordered operations 516, 518). As shown, in the section 522 illustrating a new ordered operation to be added sequentially to the existing operations set can indicate an outcome of a previous ordered operation in the operations set as the data source.

In some implementations, the particular AI agent and/or the set of AI models include instructions for extracting the medical data from the data source. The extraction can be done using natural language processing.

The particular AI agent can be selected from a variety of different types of AI agents. For example, the particular AI agent is a table agent configured to generate an electronic artifact having a table format, the particular AI agent is an abstractor agent configured to extract and standardize structured content from a medical record or an unstructured artifact; the particular AI agent is an artifact agent configured to generate a medical record artifact associated with a subject, the particular AI agent is a prompt agent configured to generate a natural language response to a query (e.g., associated with a subject that is identified in the set of instructions, the particular AI agent is a standard agent configured to generate an electronic artifact complying with a healthcare information standard.

In some implementations, the composer can be configured to provide a user with assistance with making the different selections and inputs for creating the operations set. For example, responsive to receiving the first input and the second input, the device provides a suggestion for the particular AI model from the set of AI models. The suggestion for the particular AI model can be generated, by the AI system or the device, using previously generated operations sets using the provided data source and/or the particular AI agent. The selection of the particular AI model includes accepting the suggestion for the particular AI model. In some implementations, responsive to receiving the first input, the device provides a suggestion for the particular AI agent from the set of AI agents. The suggestion for the particular AI agent is generated, by the AI system, using previously generated operations sets using the provided data source. The selection of the particular AI agent includes accepting the suggestion for the particular AI agent. In some implementations, responsive to receiving the first input, the second input, and/or the third input, the device provides a suggestion for the set of instructions. The suggestion for the set of instructions is generated, by the AI system, using previously generated operations sets using the provided data source, the particular AI agent, and/or the particular AI model. The fourth input can include accepting the suggestion for the set of instructions.

As an example, responsive to the user providing the data source, the device can generate suggestions for the AI model and the AI agent to be used. As another example, responsive to the user providing the data source, AI agent and/or the AI model selection, the device can generate a suggestion for the set of instructions.

In some implementations, the device can be configured to receive an input providing a name and a description for the ordered operation in the operations set process (e.g., the interface elements 502 and 504) and provide suggestions for one or more of the AI agent, AI model, the set of instructions and the data source. The device can also be configured to define one or more of the AI agent, AI model, the set of instructions and the data source automatically in response to the name and description received. For example, the AI system can analyze the intent for the operations set based on the name and the description, and generate the operations set based on the intent. A user can then either approve, disapprove, or edit the generated operations set.

In some implementations, the suggestion for the particular AI model is generated based on an evaluation of AI models in the set of AI models with cost, accuracy, a size of source data, and/or latency (e.g., a time delay between input being provided and output being generated). The evaluation can be performed, for example, by human review, an AI review, or a combination thereof. The evaluation can include quantitative measurements based on auxiliary datasets and/or metrics including, for example, AI review, human annotation, and/or other deterministic metrics.

In some implementations, subsequent to generating the ordered operation for the operations set, the device provides an inspection user interface (e.g., similar to as described with respect to the inspection section 408 in FIG. 4B) including a first portion including an example electronic artifact generated by the AI system using the ordered operation for the operations set. The example electronic artifact includes content generated using the data source and the set of instructions. The inspection user interface can also include a second portion including a view of content extracted from the data source that was used to generate the example electronic artifact. The inspection user interface can enable a user to inspect the example electronic artifact against the content extracted from the data source.

In some implementations, an inspection user interface is provided automatically in response to generating the ordered operation for the operations set and include an automatic evaluation (e.g., generated by the AI system) indicating, for example, whether the operations set is accurate or cost-effective.

In some implementations, the device receives an additional input that includes a description and/or name for the ordered operation for the operations set for generating an electronic artifact. The device can generate, using the description and/or the name by the AI system, suggestions for at least a portion of the data source, the particular AI agent, the particular AI model, and the set of instructions. The first input, the second input, the third input, and/or the fourth input can include accepting the suggestions of the at least a portion of the data source, the particular AI agent, the particular AI model, and the set of instructions.

In some implementations, the operations sets generated by the composer of process 900 can be shared within the platform 100. For example, there can be an application that allows a user to search for and retrieve operations sets generated by other users or the organization administrating the platform 100.

Figure 9:
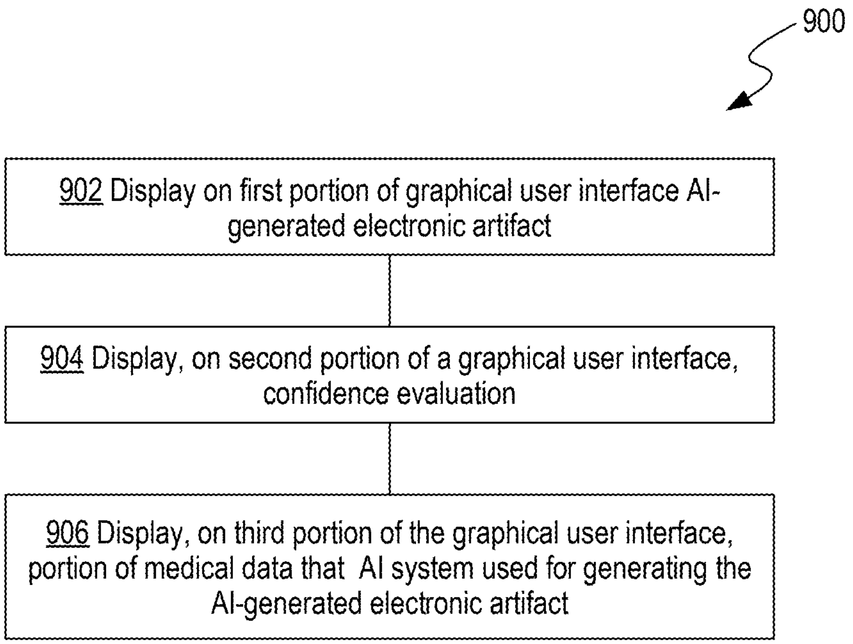
FIG. 9 is a flow diagram illustrating a process for providing artifact inspection using an AI model, in accordance with some implementations of the present technology.

FIG. 9 is a flow diagram illustrating a process 900 for providing an artifact inspection using an AI model. The process 900 can be performed by a computing device or a system (e.g., a computer system 1400 described with respect to FIG. 14). The process 900 can include displaying a graphical user interface such as the user interfaces described with respect to FIGS. 4A and 4B. The process 900 is directed to reviewing healthcare artifacts generated using AI (e.g., by the operations set processes described above). As explained, a lack of transparency and traceability in AI operations sets can lead to inaccuracies and errors that are difficult to detect. The process 900 provides a user interface for displaying an AI-generated electronic artifact that is created using, for example, user data for a subject and a set of instructions (e.g., a prompt). The AI-generated electronic artifact can include a medical status (or a user status including, e.g., a medical status or other health-related status) and a confidence evaluation indicating the accuracy or quality of the medical status, as well as compliance with healthcare regulations. Further, the user interface can provide the specific user data (e.g., user data including medical data, personal data or other health-care related data) used by the AI system to create the electronic artifact, thereby allowing the user to inspect the artifact's accuracy efficiently.

At 902, the device can display, on a first portion of a graphical user interface, an AI-generated electronic artifact (e.g., the note section 412 of the user interface 400 in FIGS. 4A and 4B). The AI-generated electronic artifact is created, by an AI system, using an input including medical data associated with a subject from a data source and a set of instructions (e.g., by an operations set generated by the composer of process 800 described with respect to FIG. 8). The AI-generated electronic artifact can indicate a medical status for the subject created using the medical data. The medical status can identify a medical condition (or a user condition including e.g., a medical condition or other health-related condition) for the subject. In some implementations, the AI-generated electronic artifact includes a medical report, clinical notes, a prescription, a treatment plan, a consent form, an insurance artifact, or a legal artifact.

At 904, the device can display, on a second portion of a graphical user interface (e.g., the confidence level section 410 in FIG. 4B), a confidence evaluation. The confidence evaluation can include a numerical value generated by the AI system using the medical data associated with the subject and historical medical status data. The confidence evaluation can be related to the accuracy or quality of the medical status or treatment of the subject.

At 906, responsive to an input on an interface element (e.g., the interface element 414 in FIG. 4B) associated with the medical condition on the first portion of the graphical user interface, the device can display, on a third portion (e.g., the inspection section 408 in FIG. 4B) of the graphical user interface, a portion of the medical data that the AI system used for generating the AI-generated electronic artifact. Displaying the AI-generated electronic artifact and the portion of the medical data can enable a user to inspect the accuracy of the AI-generated electronic artifact.

In some implementations, the AI-generated electronic artifact includes a utilization review providing information about the care of the subject at a healthcare facility, and the medical data includes a description of the subject's symptoms, user status (e.g., user status of a subject including medical status of a subject), treatment, and/or care instructions. Utilization reviews can be used for a variety of evaluation processes by healthcare-associated entities. For example, utilization reviews are used to assess the necessity, appropriateness, and efficiency of medical services and treatments by healthcare providers.

In some implementations, the confidence evaluation is further generated by comparing the medical data associated with the subject to healthcare guidelines or requirements by insurance companies, healthcare facilities, and/or healthcare officials. The confidence evaluation can depict whether the subject's medical status, treatment, and/or care instructions of the subject are in compliance with the healthcare guidelines and requirements and/or in line with medical subject matter expert judgements. The confidence evaluation can be a value within a range (e.g., a percentage). The value can be associated with predefined threshold values. For example, if the confidence evaluation is below a certain threshold value, the system flags the evaluation to a user who can further review the utilization review and/or take action.

In some implementations, in an instance that the utilization review indicates that the subject's medical status, treatment, and/or care instructions of the subject are not in compliance with the healthcare guidelines or requirements and/or in line with medical subject matter expert judgements, the portion of the medical data that the AI system used for the AI-generated electronic artifact includes specific text extracted from the healthcare guidelines and requirements that the medical status, treatment, and/or care instructions of the subject are not in compliance with. The specific text can further be highlighted or flagged (e.g., by an icon, color, pattern, or shading) to the user. Similarly, displaying the portion of the medical data that was used for the utilization review can include displaying an emphasis on the portion of the medical data that the AI system used for the AI-generated electronic artifact.

In some implementations, the AI-generated electronic artifact includes a description of the medical status for the subject, and the medical data includes a medical record associated with the subject. The medical record can be retrieved from a database including subject records.

In some implementations, the device can further display, on the graphical user interface, an AI assistant interface element for inputting instructions that cause the AI system to modify the AI-generated electronic artifact, generate additional content to the electronic artifact, or answer questions regarding the electronic artifact. A user can provide instructions on the AI assistant interface element (e.g., similar to the interface element 302 in FIG. 3A) that cause modifications and/or additions to the content of the AI-generated electronic artifact.

In some implementations, the AI-generated electronic artifact is at least partially created using the operations set generated by the process 800 described with respect to FIG. 8. In some implementations, the device can further display, on the graphical user interface, an interface element for inspecting the operations set used for creating the AI-generated electronic artifact; and responsive to receiving an input on the interface element, display a representation of the operations set.

Figure 10:
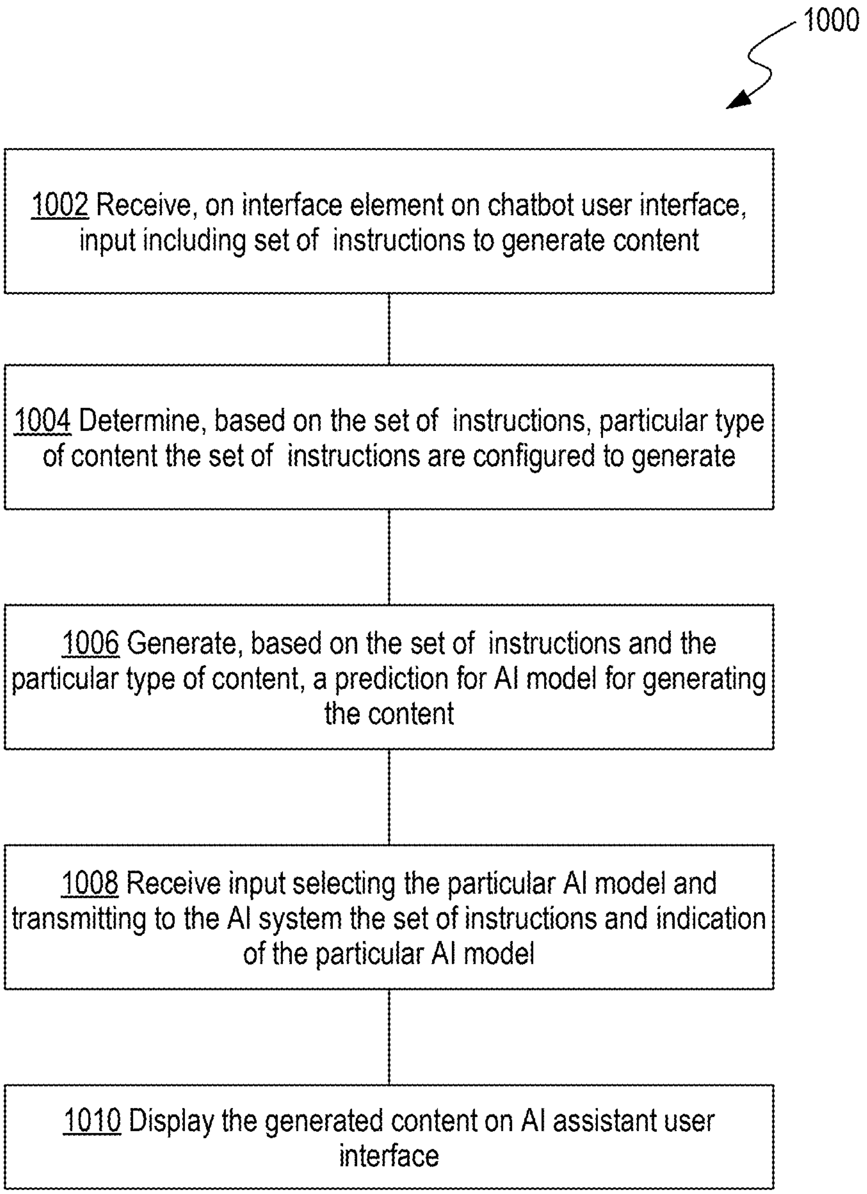
FIG. 10 is a flow diagram illustrating a process for providing an AI assistant application for healthcare, in accordance with some implementations of the present technology.

FIG. 10 is a flow diagram illustrating a process 1000 for providing an AI assistant application for healthcare. The process 1000 can be performed by a computing device or a system (e.g., a computer system 1400 described with respect to FIG. 14). The process 1000 can include displaying a graphical user interface such as the user interfaces described with respect to FIGS. 3A and 3B.

At 1002, the device can receive, on an interface element on an AI assistant user interface (e.g., the interface element 302 of the AI assistant user interface 300), an input including a set of instructions to generate content by an AI system.

At 1004, the device can determine, based on the set of instructions, a particular type of content the set of instructions are configured to generate. The set of instructions can be configured to request information, answer a question, make a decision, summarize, format, or expand content, analyze or evaluate information or data, etc. The type of content to be generated is dependent on the set of instructions.

At 1006, the device can generate, based on the set of instructions and the particular type of content, a suggestion for an AI model (e.g., a language model (LM)) for generating the content by the AI system. The suggestion for the AI model can indicate a particular AI model of a set of pre-defined AI models. Each of the set of pre-defined AI models can be evaluated for multiple types of content (e.g., to provide a value describing how good a respective AI model is for generating different types of content). The multiple types of content can include a particular type of content. The evaluation can be performed using historical AI-generated content generated by the set of pre-defined AI models. In some implementations, the evaluation is performed using a set of parameters including cost, accuracy, size of source content, and/or latency.

At 1008, the device can receive, on the AI assistant user interface, an input selecting the particular AI model and transmitting to the AI system the set of instructions and an indication of the particular AI model. The AI system can be configured to generate the content using the particular AI model and the set of instructions. At 1010, the device can display the generated content on the AI assistant user interface.

In some implementations, the content is generated, by the AI system, using source content extracted from a data source. The device can display, concurrently with displaying the generated content on the AI assistant user interface, an inspection section including at least a portion of the source content extracted from the data source used for generating the content. The inspection section can be similar to the inspection section 08 described with respect to FIG. 4B. The device can display the at least a portion of the source content extracted from the data source used for generating the content thereby enabling a user to inspect the accuracy of the AI-generated electronic artifact. The inspection section can increase the traceability and transparency to the operation of the AI assistant and allow a user to more easily evaluate the accuracy of the content generated by the AI.

In some implementations, it is further determined whether the set of instructions includes the sensitive information. Sensitive information can refer to information that should be protected, e.g., based on regulations and laws, from unauthorized access due to its confidential, personal, or proprietary nature. Sensitive information can include social security numbers, personal information, health information, etc. In some implementations, responsive to a determination that the set of instructions includes particular text associated with sensitive information, an obfuscated set of instructions is generated by substituting the particular text with a particular token (e.g., a meaningless, random set of symbols, letters, numbers, or a combination thereof). In such implementations, transmitting to the AI system the set of instructions includes transmitting the obfuscated set of instructions. The AI system can be configured to generate the content, prior to displaying the generated content on the AI assistant user interface, by generating obfuscated content using the obfuscated set of instructions. The obfuscated content can include the particular token. The obfuscated content can be then de-obfuscated by substituting the particular token with the particular text associated with the sensitive information to form the generated content. The obfuscation and de-obfuscation can be performed by the system and process described with respect to FIGS. 11A through 11E.

In some implementations, displaying the generated content on the AI assistant user interface comprises displaying the particular text with a visual indicator indicating that the particular text comprises sensitive information (e.g., as shown in FIG. 11D).

Figure 11A:
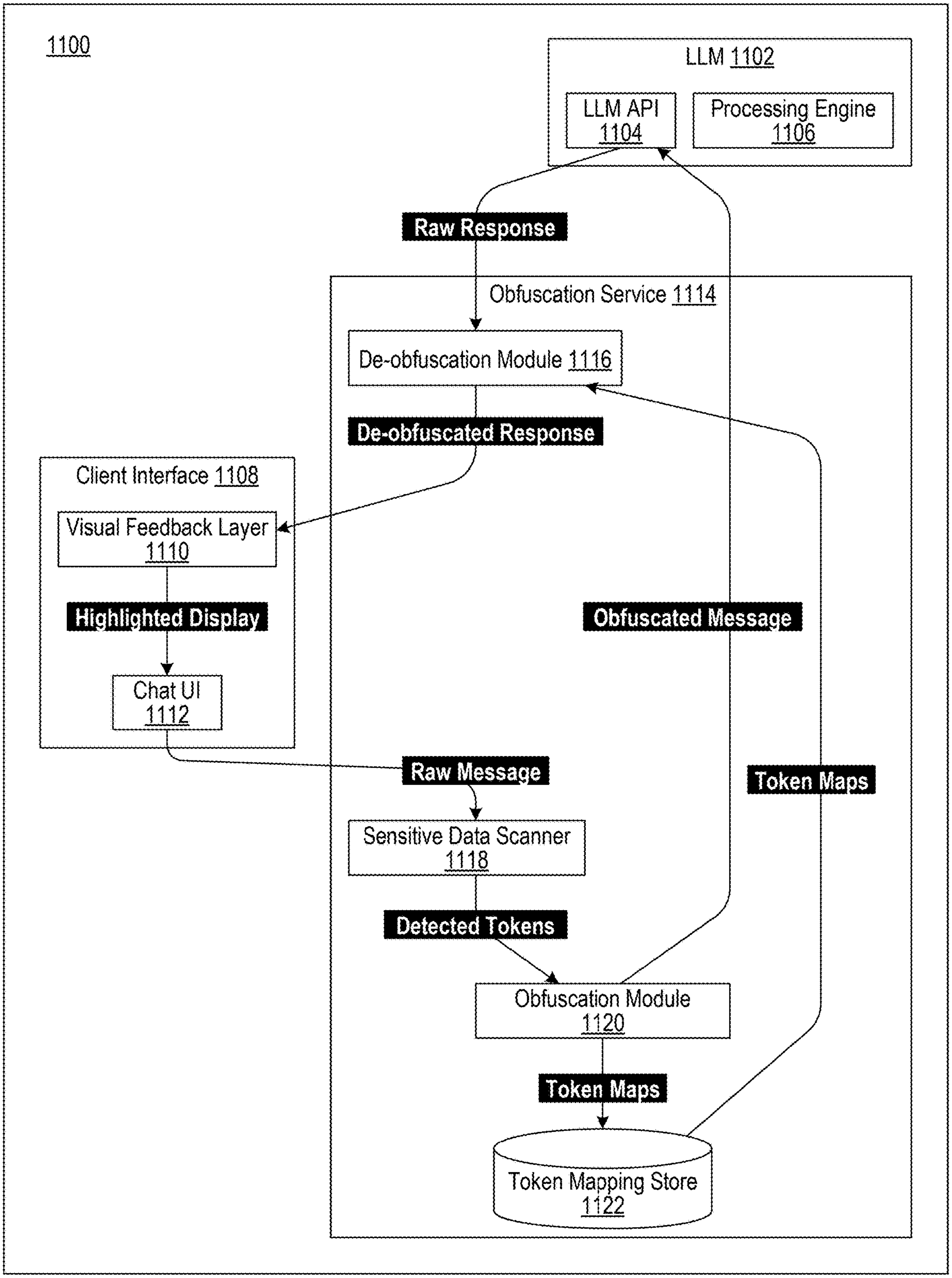
Figure 11B:
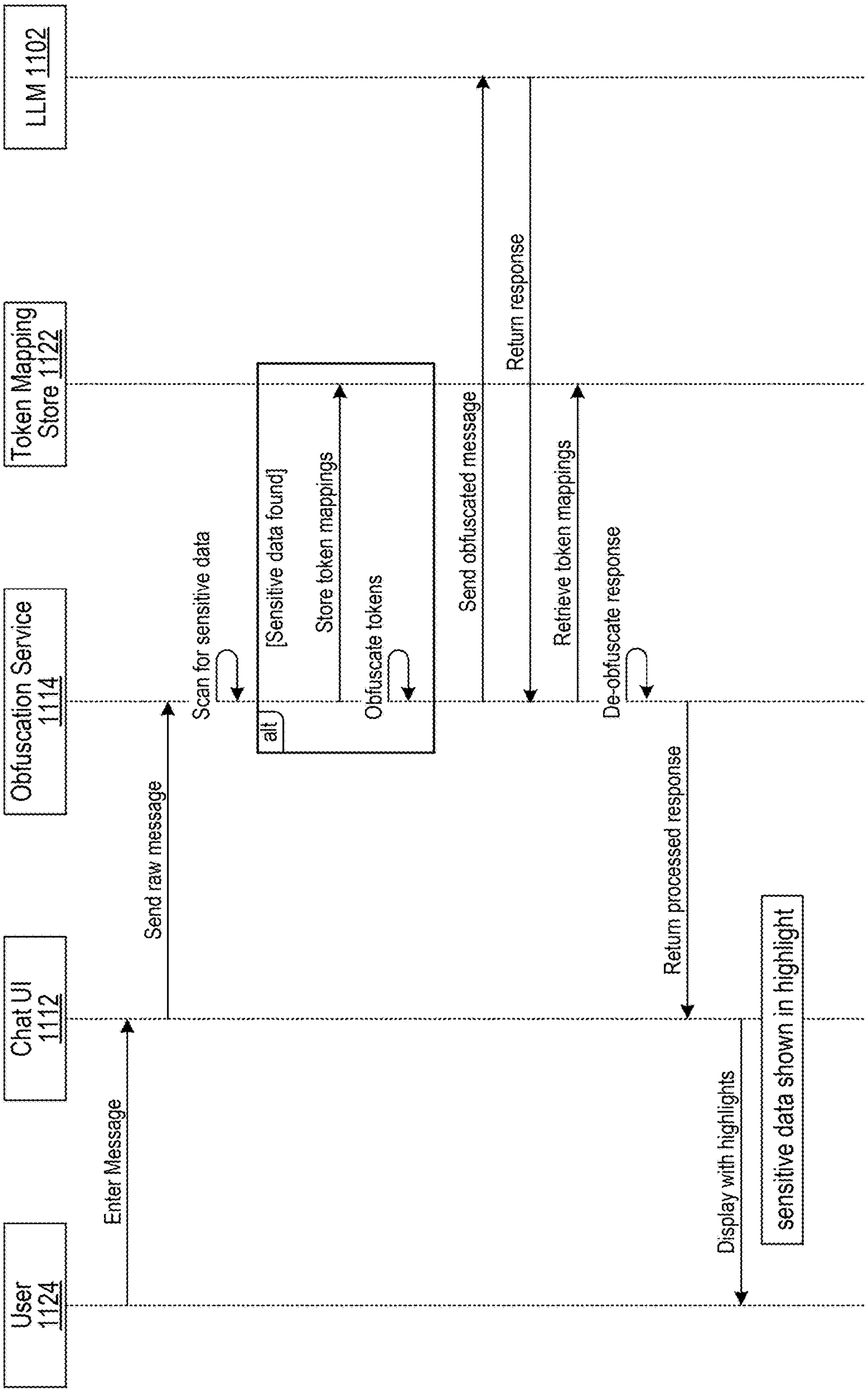

In some implementations, generating the obfuscated set of instructions comprises generating a token mapping that associates the particular text to the particular token, and the generated token mapping is stored in a token mapping data store (e.g., as described with respect to FIGS. 11A and 11B). In some implementations, de-obfuscating the obfuscated content comprises retrieving a token mapping that associates the particular text to the particular token from a token mapping data store.

System and Method for Obfuscation and De-Obfuscation of Sensitive Information

Transmission of sensitive information to AI systems can be associated with privacy and security risks. Conventional solutions for protection of sensitive information either completely restrict sensitive data or rely on manual redaction, lacking automated, reversible protection mechanisms. The process and system described herein provides for automatically detecting, obfuscating, and de-obfuscating sensitive information in real-time communications with AI models, such as LLM models (e.g., as described with respect to FIGS. 12 and 13) while maintaining conversation coherence and providing visual feedback to users. The process and system for real-time obfuscation and de-obfuscation can be applied to any of the processes described in this disclosure, including the processes described with respect to FIGS. 8 through 10.

FIGS. 11A through 11E illustrate processes and interfaces for obfuscation and de-obfuscation of sensitive information, in accordance with some implementations of the present technology. A system configured for obfuscation and de-obfuscation can provide real-time reversible obfuscation of sensitive information and a visual feedback system that indicates obfuscated content. The system can ensure the maintenance of conversation coherence by handling tokens consistently and incorporates automated detection and classification of sensitive information. Additionally, the solution is designed for seamless integration with existing LLM systems and platforms.

The system can provide enhanced privacy protection for sensitive user data (e.g., user data including medical data, personal data, and/or other healthcare-related data) and promote transparency in data handling through the visual feedback mechanism. The utility of LLM responses can be maintained, while the risk of sensitive information exposure is reduced. Furthermore, the system can support scalable implementation across various LLM platforms.

The system can be applied to a variety of industries, including healthcare communication systems, financial services chatbots, legal document processing, human resources applications, and customer service platforms.

In the various implementations, certain considerations can be addressed. For example, selection of appropriate encryption methods for storing token mappings, performance of real-time processing, ensuring of the scalability of the token storage system, integration with different LLM APIs, and maintaining the security of the obfuscation and deobfuscation processes.

A system configured for obfuscation and de-obfuscation can include a GUI (e.g., a client interface in FIG. 11A), including a chat-based interface for user interaction, visual highlighting system for obfuscated information, and a real-time display of messages and responses. The system can also include an obfuscation service system (e.g., an obfuscation service in FIG. 11A). The obfuscation service system can include a pattern recognition engine for sensitive data detection, a reversible obfuscation mechanism (e.g., hashing algorithm), a token mapping and storage system, and de-obfuscation capability for processed responses. The system includes, or is in communication with, an LLM system (e.g., the LLM system 1300 described with respect to FIG. 13). The LLM system can include a message streaming interface, a response handling system, and a token preservation mechanism. In some implementations, the system is configured to perform an embedding service. As an example, a document uploaded via the GUI can be converted to a plain text format. The document can be processed to divide the document into portions (e.g., chunks) consisting of a predefined number of tokens. Embeddings can be generated for each portion and stored in a vector database.

In some embodiments, the system can be configured to perform an artifact query service. As an example, queries received via the user interface are embedded using the same mode as used in the embedding service. A query embedding can be scored against entries from the vector database generated by the embedding service. The top-k portions with the highest scores are selected and returned to the client interface.

A method for obfuscating and de-obfuscating sensitive data can include input processing. For example, a user can input a message in a chat interface (e.g., FIGS. 3A and 3B). The message can be intercepted by the obfuscation service system, which scans the input for predefined categories of sensitive information.

The obfuscation processing can include identifying sensitive tokens using classification rules. Tokens can be obfuscated using reversible transformation. Original tokens and their obfuscated versions can be mapped and stored. The obfuscation processing also includes generating a modified message for LLM processing. The generated modified message (e.g., an obfuscated message) can be transmitted to the LLM system. The LLM system processes the modified message and generates a response. The response maintains obfuscation of the sensitive tokens. The response is then processed by the obfuscation service to be de-obfuscated. The obfuscated tokens are restored using stored mappings. The de-obfuscated message can be displayed on the GUI so that the sensitive information in the message is highlighted with a visual indicator (e.g., with a color, a pattern, or a highlight). Visual indicators can be used to indicate which portions were protected during the obfuscation/de-obfuscation process.

The obfuscation and de-obfuscation method can be applied to artifacts. For example, a user can upload an artifact that they want to interact with in the chat interface. In such an instance, the artifact can be transmitted to the embedding service and relevant embeddings can be stored in a vector database. A query can be received via the user interface and sent to the artifact query service to retrieve relevant portions of the artifact. The query and retrieved portions can be sent to the obfuscation service, and further, the obfuscated query and portions can be sent to the LLM. A message returned by the LLM is deobfuscated and sent to the user interface.

FIG. 11A illustrates a system architecture diagram illustrating the primary components of the real-time sensitive information protection system 1100. The diagram shows three main subsystems: (1) a client interface 1108, comprising the chat UI 1112 and a visual feedback layer 1110; (2) an obfuscation service 1114 (e.g., corresponding to the obfuscation tool 124 described with respect to FIG. 1), containing the sensitive data scanner 1118, obfuscation module 1120, token mapping store 11212, and de-obfuscation module 1116; and (3) an LLM system 1102 including an LLM API 1104 and a processing engine 1106. In FIG. 11A, arrows indicate data flow between the components, with raw messages being processed through the obfuscation pipeline before reaching the LLM and responses following the reverse path through de-obfuscation.

FIG. 11B illustrates a message processing sequence diagram depicting the temporal flow of information through the system 1100. The diagram illustrates the interaction between a user, the chat UI 1112, the obfuscation service 1114, the token mapping store 1122, and the LLM 1102 system during a message exchange. The sequence includes the detection of sensitive information, token mapping storage, obfuscation process, LLM interaction, and subsequent de-obfuscation steps, culminating in the display of processed responses with appropriate highlighting of protected information to the end user.

Figure 11C:
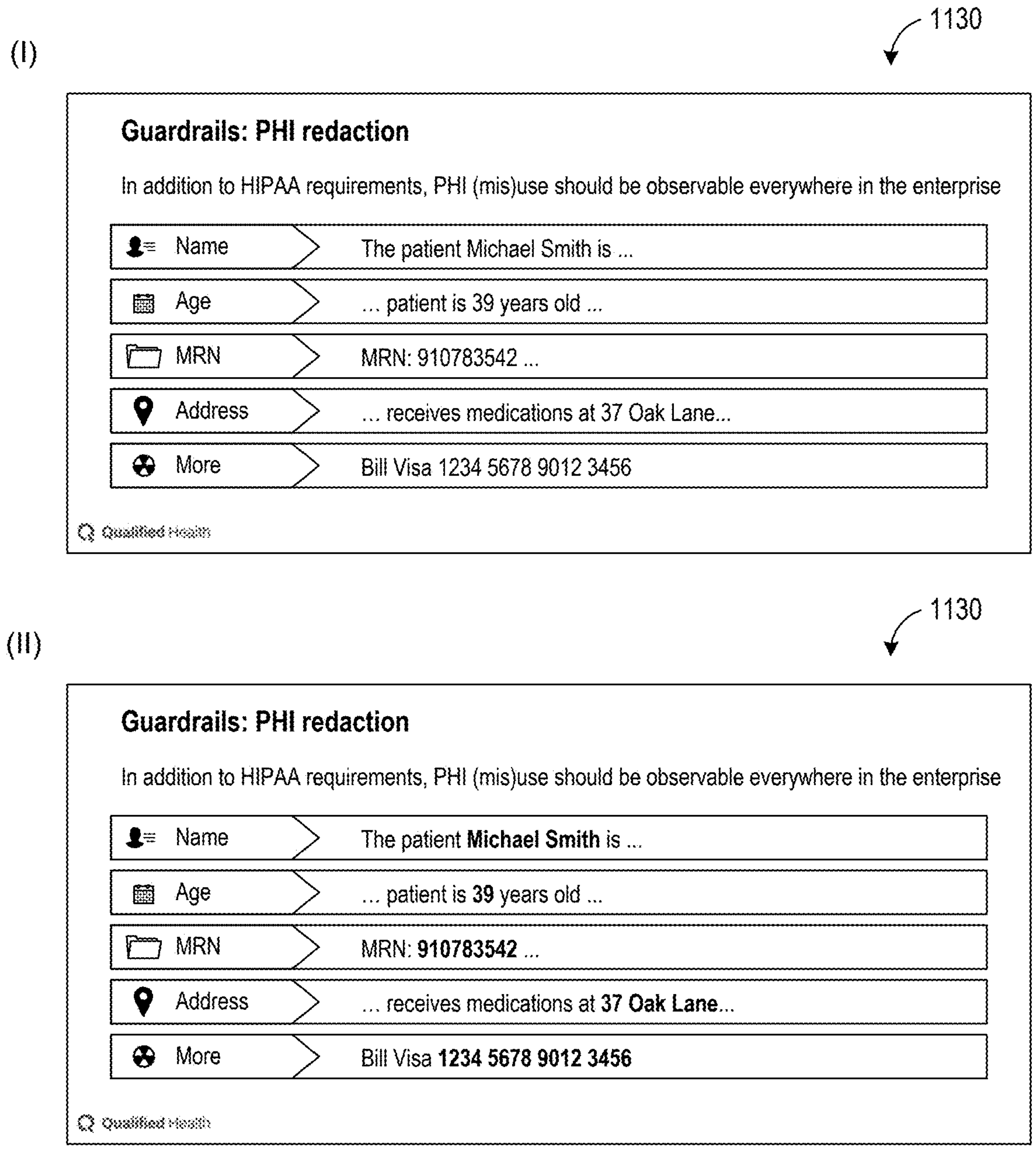

FIG. 11C, section (I), illustrates a user interface 1130 displaying patient health information (PHI) prior to automated detection, showing various fields including name, age, medical record number (MRN), address, and payment information in their raw, unprocessed form. The GUI can demonstrate a standard presentation of sensitive healthcare data within an enterprise system.

FIG. 11C, section (II), illustrates the same user interface 1130 after PHI detection and highlighting, demonstrating automated identification of sensitive information. The PHI elements are visually indicated (e.g., including patient name (Michael Smith), age (39), MRN (910783542), address (37 Oak Lane), and payment information (credit card number). The visual indication illustrates the system's capability to identify and visually flag multiple categories of protected health information in accordance with HIPAA requirements.

FIG. 11D, section (I), illustrates an exemplary obfuscation of prompts with PHI going out to the LLM system. The example includes PHI detection in a clinical note summarization prompt. The visualization demonstrates identification of multiple PHI elements (shown with visual indication), including patient name, medical record number (MRN), date of birth (DOB), visit date, and provider name, while preserving the clinical content necessary for summarization. FIG. 11D, section (II) illustrates an exemplary obfuscation of prompts with PHI and protected class information going out to the LLM system. The example includes a multi-category sensitive information detection in an administrative communication prompt. The visualization shows detection of both PHI elements (indicated with a first visual indication), including patient name, date of birth, SSN, and provider name, as well as protected class information (indicated with a second visual indication), including ethnicity and religious beliefs. This example demonstrates the system's capability to distinguish between different categories of sensitive information within the same message.

Figure 11E:
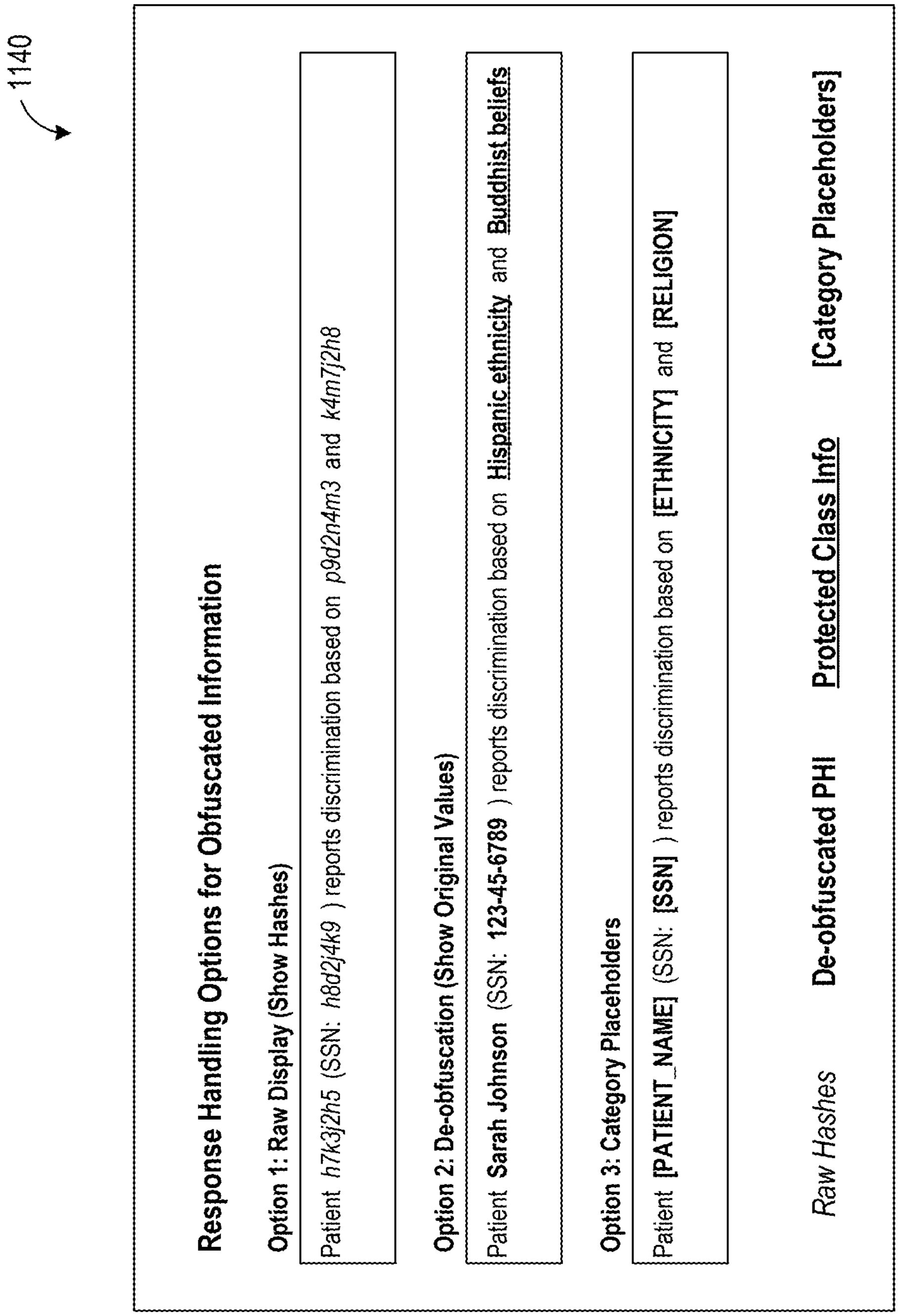

FIG. 11E illustrates a GUI 1140 with obfuscated sensitive information returned from an LLM. Response handling options for protected information illustrating three alternative methods for displaying LLM responses containing previously obfuscated sensitive data. FIG. 11E demonstrates: (1) raw display, showing the unmodified hash values as returned by the LLM; (2) de-obfuscation, where original sensitive values are recovered from the client-side hash mapping and displayed with appropriate highlighting for phi (personal health information) and protected class information; and (3) category placeholders, where hashed values are replaced with descriptive category labels (e.g., [PATIENT-_NAME], [SSN]) while maintaining visual indication. The example shows consistent handling of multiple sensitive data types, including patient identifiers, social security numbers, ethnicity, and religious beliefs, across all three display options. A legend differentiates between raw hashes, de-obfuscated PHI, protected class information, and category placeholders.

Exemplary Artificial Intelligence (AI) System

Figure 12:
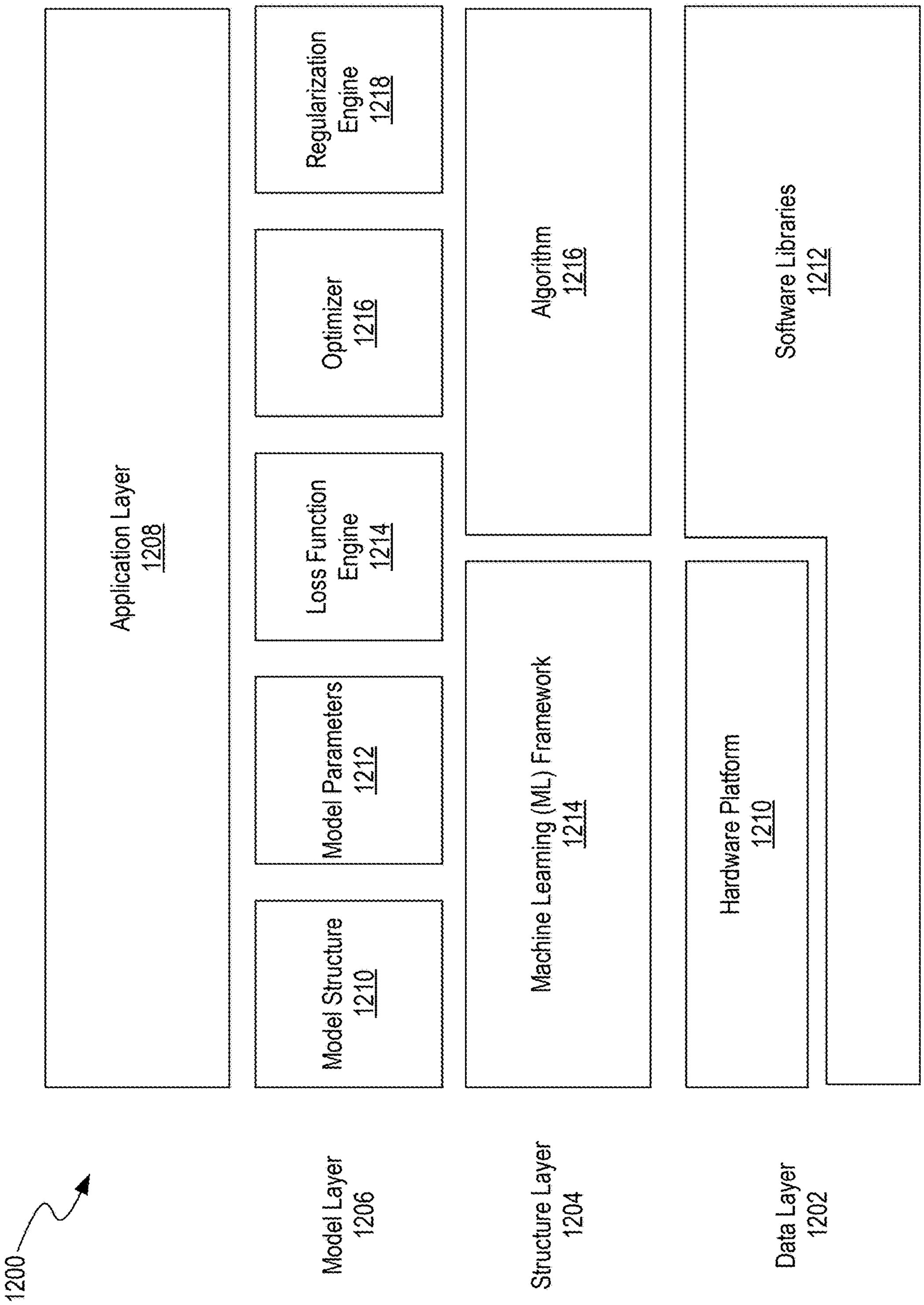
FIG. 12 illustrates a layered architecture of an AI system that can implement the machine learning (ML) models, in accordance with some implementations of the present technology.

FIG. 12 illustrates a layered architecture of an AI system 1200 that can implement the processes described above, in accordance with some implementations of the present technology. The AI system 1200 can be in communication with, or part of, the platform 100 described with respect to FIG. 1. In particular, the AI system 1200 is associated with the AI tool 104 which is configured to integrate processes performed by the AI system 1200 with the user applications 102 of the platform 100.

As shown, the AI system 1200 can include a set of layers, which conceptually organize elements within an example network topology for the AI system's architecture to implement a particular AI model. Generally, an AI model is a computer-executable program implemented by the AI system 1200 that analyses data to make predictions. Information can pass through each layer of the AI system 1200 to generate outputs for the AI model. The layers can include a data layer 1202, a structure layer 1204, a model layer 1206, and an application layer 1208. The algorithm 1216 of the structure layer 1204 and the model structure 1220 and model parameters 1222 of the model layer 1206 together form an example AI model. The optimizer 1226, loss function engine 1224, and regularization engine 1228 work to refine and optimize the AI model, and the data layer 1202 provides resources and support for application of the AI model by the application layer 1208.

The data layer 1202 acts as the foundation of the AI system 1200 by preparing data for the AI model. As shown, the data layer 1202 can include two sub-layers: a hardware platform 1210 and one or more software libraries 1212. The hardware platform 1210 can be designed to perform operations for the AI model and include computing resources for storage, memory, logic and networking (e.g., as described with respect to a computer system 1400 in FIG. 14). The hardware platform 1210 can process amounts of data using one or more servers. The servers can perform backend operations such as matrix calculations, parallel calculations, machine learning (ML) training, and the like. Examples of servers used by the hardware platform 1210 include central processing units (CPUs) and graphics processing units (GPUs). CPUs are electronic circuitry designed to execute instructions for computer programs, such as arithmetic, logic, controlling, and input/output (I/O) operations, and can be implemented on integrated circuit (IC) microprocessors. GPUs are electric circuits that were originally designed for graphics manipulation and output but may be used for AI applications due to their vast computing and memory resources. GPUs use a parallel structure that generally makes their processing more efficient than that of CPUs. In some instances, the hardware platform 1210 can include computing resources, (e.g., servers, memory, etc.) offered by a cloud services provider. The hardware platform 1210 can also include computer memory for storing data about the AI model, application of the AI model, and training data for the AI model. The computer memory can be a form of random-access memory (RAM), such as dynamic RAM, static RAM, and non-volatile RAM.

The software libraries 1212 can be thought of suites of data and programming code, including executables, used to control the computing resources of the hardware platform 1210. The programming code can include low-level primitives (e.g., fundamental language elements) that form the foundation of one or more low-level programming languages, such that servers of the hardware platform 1210 can use the low-level primitives to carry out specific operations. The low-level programming languages do not require much, if any, abstraction from a computing resource's instruction set architecture, allowing them to run quickly with a small memory footprint. Examples of software libraries 1212 that can be included in the AI system 1200 include INTEL Math Kernel Library, NVIDIA cuDNN, EIGEN, and OpenBLAS.

The structure layer 1204 can include an ML framework 1214 and an algorithm 1216. The ML framework 1214 can be thought of as an interface, library, or tool that allows users to build and deploy the AI model. The ML framework 1214 can include an open-source library, an application programming interface (API), a gradient-boosting library, an ensemble method, and/or a deep learning toolkit that work with the layers of the AI system facilitate development of the AI model. For example, the ML framework 1214 can distribute processes for application or training of the AI model across multiple resources in the hardware platform 1210. The ML framework 1214 can also include a set of pre-built components that have the functionality to implement and train the AI model and allow users to use pre-built functions and classes to construct and train the AI model. Thus, the ML framework 1214 can be used to facilitate data engineering, development, hyperparameter tuning, testing, and training for the AI model. Examples of ML frameworks 1214 that can be used in the AI system 1200 include TENSORFLOW, PYTORCH, SCIKIT-LEARN, KERAS, LightGBM, RANDOM FOREST, and AMAZON WEB SERVICES.

The algorithm 1216 can be an organized set of computer-executable operations used to generate output data from a set of input data and can be described using pseudocode. The algorithm 1216 can include complex code that allows the computing resources to learn from new input data and create new/modified outputs based on what was learned. In some implementations, the algorithm 1216 can build the AI model through being trained while running computing resources of the hardware platform 1210. This training allows the algorithm 1216 to make predictions or decisions without being explicitly programmed to do so. Once trained, the algorithm 1216 can run at the computing resources as part of the AI model to make predictions or decisions, improve computing resource performance, or perform tasks. The algorithm 1216 can be trained using supervised learning, unsupervised learning, semi-supervised learning, and/or reinforcement learning.

Using supervised learning, the algorithm 1216 can be trained to learn patterns (e.g., map input data to output data) based on labeled training data. The training data may be labeled by an external user or operator. For instance, a user may indicate a set of training data that includes, for example, historical healthcare artifacts. The historical healthcare artifacts can be labeled based on one or more classes. As an example, in an instance of a utilization review training data associated with the utilization review application 112, the training data can include historical medical records of subjects including a particular medical status and guidelines associated with the particular medical status, together with historical classifications of whether or not the medical status was complying with the guidelines. The training data is used to train the AI model by inputting the training data into the algorithm 1216. The algorithm determines how to label the new data based on the labeled training data. The user can facilitate collection, labeling, and/or input via the ML framework 1214. In some instances, the user may convert the training data to a set of feature vectors for input to the algorithm 1216. Once trained, the user can test the algorithm 1216 on new data to determine if the algorithm 1216 is predicting accurate labels for the new data. For example, the user can use cross-validation methods to test the accuracy of the algorithm 1216 and retrain the algorithm 1216 on new training data if the results of the cross-validation are below an accuracy threshold.

Supervised learning can involve classification and/or regression. Classification techniques involve teaching the algorithm 1216 to identify a category of new observations based on training data and are used when input data for the algorithm 1216 is discrete. Said differently, when learning through classification techniques, the algorithm 1216 receives training data labeled with categories (e.g., classes) and determines how features observed in the training data (e.g., various claim elements, policy identifiers, tokens extracted from unstructured data) relate to the categories (e.g., risk propensity categories, claim leakage propensity categories, complaint propensity categories). Once trained, the algorithm 1216 can categorize new data by analyzing the new data for features that map to the categories. Examples of classification techniques include boosting, decision tree learning, genetic programming, learning vector quantization, k-nearest neighbor (k-NN) algorithm, and statistical classification.

Regression techniques involve estimating relationships between independent and dependent variables and are used when input data to the algorithm 1216 is continuous. Regression techniques can be used to train the algorithm 1216 to predict or forecast relationships between variables. To train the algorithm 1216 using regression techniques, a user can select a regression method for estimating the parameters of the model. The user collects and labels training data that is input to the algorithm 1216 such that the algorithm 1216 is trained to understand the relationship between data features and the dependent variable(s). Once trained, the algorithm 1216 can predict missing historic data or future outcomes based on input data. Examples of regression methods include linear regression, multiple linear regression, logistic regression, regression tree analysis, least squares method, and gradient descent. In an example implementation, regression techniques can be used, for example, to estimate and fill-in missing data for machine-learning based pre-processing operations.

Under unsupervised learning, the algorithm 1216 learns patterns from unlabeled training data. In particular, the algorithm 1216 is trained to learn hidden patterns and insights of input data, which can be used for data exploration or for generating new data. Here, the algorithm 1216 does not have a predefined output, unlike the labels output when the algorithm 1216 is trained using supervised learning. Said another way, unsupervised learning is used to train the algorithm 1216 to find an underlying structure of a set of data, group the data according to similarities, and represent that set of data in a compressed format.

A few techniques can be used in supervised learning: clustering, anomaly detection, and techniques for learning latent variable models. Clustering techniques involve grouping data into different clusters that include similar data, such that other clusters contain dissimilar data. For example, during clustering, data with possible similarities remain in a group that has less or no similarities to another group. Examples of clustering techniques density-based methods, hierarchical based methods, partitioning methods, and grid-based methods. In one example, the algorithm 1216 may be trained to be a k-means clustering algorithm, which partitions n observations in k clusters such that each observation belongs to the cluster with the nearest mean serving as a prototype of the cluster. Anomaly detection techniques are used to detect previously unseen rare objects or events represented in data without prior knowledge of these objects or events. Anomalies can include data that occur rarely in a set, a deviation from other observations, outliers that are inconsistent with the rest of the data, patterns that do not conform to well-defined normal behavior, and the like. When using anomaly detection techniques, the algorithm 1216 may be trained to be an Isolation Forest, local outlier factor (LOF) algorithm, or K-nearest neighbor (k-NN) algorithm. Latent variable techniques involve relating observable variables to a set of latent variables. These techniques assume that the observable variables are the result of an individual's position on the latent variables and that the observable variables have nothing in common after controlling for the latent variables. Examples of latent variable techniques that may be used by the algorithm 1216 include factor analysis, item response theory, latent profile analysis, and latent class analysis.

The model layer 1206 implements the AI model using data from the data layer and the algorithm 1216 and ML framework 1214 from the structure layer 1204, thus enabling decision-making capabilities of the AI system 1200. The model layer 1206 includes a model structure 1220, model parameters 1222, a loss function engine 1224, an optimizer 1226, and a regularization engine 1228.

The model structure 1220 describes the architecture of the AI model of the AI system 1200. The model structure 1220 defines the complexity of the pattern/relationship that the AI model expresses. Examples of structures that can be used as the model structure 1220 include decision trees, support vector machines, regression analyses, Bayesian networks, Gaussian processes, genetic algorithms, and artificial neural networks (or, simply, neural networks). The model structure 1220 can include a number of structure layers, a number of nodes (or neurons) at each structure layer, and activation functions of each node. Each node's activation function defines how to node converts data received to data output. The structure layers may include an input layer of nodes that receive input data, an output layer of nodes that produce output data. The model structure 1220 may include one or more hidden layers of nodes between the input and output layers. The model structure 1220 can be an Artificial Neural Network (or, simply, neural network) that connects the nodes in the structured layers such that the nodes are interconnected. Examples of neural networks include Feedforward Neural Networks, convolutional neural networks (CNNs), Recurrent Neural Networks (RNNs), Autoencoder, and Generative Adversarial Networks (GANs).

The model parameters 1222 represent the relationships learned during training and can be used to make predictions and decisions based on input data. The model parameters 1222 can weight and bias the nodes and connections of the model structure 1220. For instance, when the model structure 1220 is a neural network, the model parameters 1222 can weight and bias the nodes in each layer of the neural networks, such that the weights determine the strength of the nodes, and the biases determine the thresholds for the activation functions of each node. The model parameters 1222, in conjunction with the activation functions of the nodes, determine how input data is transformed into desired outputs. The model parameters 1222 can be determined and/or altered during training of the algorithm 1216.

The loss function engine 1224 can determine a loss function, which is a metric used to evaluate the AI model's performance during training. For instance, the loss function engine 1224 can measure the difference between a predicted output of the AI model and the actual output of the AI model and is used to guide optimization of the AI model during training to minimize the loss function. The loss function may be presented via the ML framework 1214, such that a user can determine whether to retrain or otherwise alter the algorithm 1216 if the loss function is over a threshold. In some instances, the algorithm 1216 can be retrained automatically if the loss function is over the threshold. Examples of loss functions include a binary-cross entropy function, hinge loss function, regression loss function (e.g., mean square error, quadratic loss, etc.), mean absolute error function, smooth mean absolute error function, log-cosh loss function, and quantile loss function.

The optimizer 1226 adjusts the model parameters 1222 to minimize the loss function during training of the algorithm 1216. In other words, the optimizer 1226 uses the loss function generated by the loss function engine 1224 as a guide to determine what model parameters lead to the most accurate AI model. Examples of optimizers include Gradient Descent (GD), Adaptive Gradient Algorithm (AdaGrad), Adaptive Moment Estimation (Adam), Root Mean Square Propagation (RMSprop), Radial Base Function (RBF) and Limited-memory BFGS (L-BFGS). The type of optimizer 1226 used may be determined based on the type of model structure 1220 and the size of data and the computing resources available in the data layer 1202.

The regularization engine 1228 executes regularization operations. Regularization is a technique that prevents over- and under-fitting of the AI model. Overfitting occurs when the algorithm 1216 is overly complex and too adapted to the training data, which can result in poor performance of the AI model. Underfitting occurs when the algorithm 1216 is unable to recognize even basic patterns from the training data such that it cannot perform well on training data or on validation data. The optimizer 1226 can apply one or more regularization techniques to fit the algorithm 1216 to the training data properly, which helps constraint the resulting AI model and improves its ability for generalized application. Examples of regularization techniques include lasso (L1) regularization, ridge (L2) regularization, and elastic (L1 and L2 regularization).

The application layer 1208 describes how the AI system 1200 is used to solve problem or perform tasks.

Transformer for Neural Network

To assist in understanding the present disclosure, some concepts relevant to neural networks and ML are discussed herein. Generally, a neural network comprises a number of computation units (sometimes referred to as "neurons"). Each neuron receives an input value and applies a function to the input to generate an output value. The function typically includes a parameter (also referred to as a "weight") whose value is learned through the process of training. A plurality of neurons may be organized into a neural network layer (or simply "layer") and there may be multiple such layers in a neural network. The output of one layer may be provided as input to a subsequent layer. Thus, input to a neural network may be processed through a succession of layers until an output of the neural network is generated by a final layer. This is a simplistic discussion of neural networks and there may be more complex neural network designs that include feedback connections, skip connections, and/or other such possible connections between neurons and/or layers, which are not discussed in detail here.

A deep neural network (DNN) is a type of neural network having multiple layers and/or a large number of neurons.

The term DNN can encompass any neural network having multiple layers, including convolutional neural networks (CNNs), recurrent neural networks (RNNs), multilayer perceptrons (MLPs), Generative Adversarial Networks (GANs), Variational Autoencoders (VAEs), and Auto-regressive Models, among others. Unlike discriminative models, generative models are distinguished by their ability to create new, synthetic data that closely resembles the training data. In contrast, discriminative models focus on predicting labels for given inputs.

DNNs are often used as ML-based models for modeling complex behaviors (e.g., human language, image recognition, object classification) in order to improve the accuracy of outputs (e.g., more accurate predictions) such as, for example, as compared with models with fewer layers. In the present disclosure, the term "ML-based model" or more simply "ML model" may be understood to refer to a DNN. Training an ML model refers to a process of learning the values of the parameters (or weights) of the neurons in the layers such that the ML model is able to model the target behavior to a desired degree of accuracy. Training typically requires the use of a training dataset, which is a set of data that is relevant to the target behavior of the ML model.

As an example, to train an ML model that is intended to model human language (also referred to as a "language model"), the training dataset may be a collection of text documents, referred to as a "text corpus" (or simply referred to as a "corpus"). The corpus may represent a language domain (e.g., a single language), a subject domain (e.g., scientific papers), and/or may encompass another domain or domains, be they larger or smaller than a single language or subject domain. For example, a relatively large, multilingual, and non-subject-specific corpus can be created by extracting text from online webpages and/or publicly available social media posts. Training data can be annotated with ground truth labels (e.g., each data entry in the training dataset can be paired with a label) or may be unlabeled.

Training an ML model generally involves inputting into an ML model (e.g., an untrained ML model) training data to be processed by the ML model, processing the training data using the ML model, collecting the output generated by the ML model (e.g., based on the inputted training data), and comparing the output to a desired set of target values. If the training data is labeled, the desired target values may be, e.g., the ground truth labels of the training data. If the training data is unlabeled, the desired target value may be a reconstructed (or otherwise processed) version of the corresponding ML model input (e.g., in the case of an autoencoder), or can be a measure of some target observable effect on the environment (e.g., in the case of a reinforcement learning agent). The parameters of the ML model are updated based on a difference between the generated output value and the desired target value. For example, if the value outputted by the ML model is excessively high, the parameters may be adjusted so as to lower the output value in future training iterations. An objective function is a way to quantitatively represent how close the output value is to the target value. An objective function represents a quantity (or one or more quantities) to be optimized (e.g., minimize a loss or maximize a reward) in order to bring the output value as close to the target value as possible. The goal of training the ML model typically is to minimize a loss function or maximize a reward function.

The training data can be a subset of a larger data set. For example, a data set may be split into three mutually exclusive subsets: a training set, a validation (or cross-validation) set, and a testing set. The three subsets of data may be used sequentially during ML model training. For example, the training set may be first used to train one or more ML models, each ML model, e.g., having a particular architecture, having a particular training procedure, being describable by a set of model hyperparameters, and/or otherwise being varied from the other of the one or more ML models. The validation (or cross-validation) set may then be used as input data into the trained ML models to, e.g., measure the performance of the trained ML models and/or compare performance between them. Where hyperparameters are used, a new set of hyperparameters can be determined based on the measured performance of one or more of the trained ML models, and the first ordered operation of training (e.g., with the training set) may begin again on a different ML model described by the new set of determined hyperparameters. In this way, these ordered operations can be repeated to produce a more performant trained ML model. Once such a trained ML model is obtained (e.g., after the hyperparameters have been adjusted to achieve a desired level of performance), a third ordered operation of collecting the output generated by the trained ML model applied to the third subset (the testing set) may begin. The output generated from the testing set may be compared with the corresponding desired target values to give a final assessment of the trained ML model's accuracy. Other segmentations of the larger data set and/or schemes for using the segments for training one or more ML models are possible.

Backpropagation is an algorithm for training an ML model. Backpropagation is used to adjust (e.g., update) the value of the parameters in the ML model, with the goal of optimizing the objective function. For example, a defined loss function is calculated by forward propagation of an input to obtain an output of the ML model and a comparison of the output value with the target value. Backpropagation calculates a gradient of the loss function with respect to the parameters of the ML model, and a gradient algorithm (e.g., gradient descent) is used to update (e.g., "learn") the parameters to reduce the loss function. Backpropagation is performed iteratively so that the loss function is converged or minimized. Other techniques for learning the parameters of the ML model can be used. The process of updating (or learning) the parameters over many iterations is referred to as training. Training may be carried out iteratively until a convergence condition is met (e.g., a predefined maximum number of iterations has been performed, or the value outputted by the ML model is sufficiently converged with the desired target value), after which the ML model is considered to be sufficiently trained. The values of the learned parameters can then be fixed and the ML model may be deployed to generate output in real-world applications (also referred to as "inference").

In some examples, a trained ML model may be fine-tuned, meaning that the values of the learned parameters may be adjusted slightly in order for the ML model to better model a specific task. Fine-tuning of an ML model typically involves further training the ML model on a number of data samples (which may be smaller in number/cardinality than those used to train the model initially) that closely target the specific task. For example, an ML model for generating natural language that has been trained generically on publicly available text corpora may be, e.g., fine-tuned by further training using specific training samples. The specific training samples can be used to generate language in a certain style or in a certain format. For example, the ML model can be trained to generate a blog post having a particular style and structure with a given topic.

Some concepts in ML-based language models are now discussed. It may be noted that, while the term "language model" has been commonly used to refer to an ML-based language model, there could exist non-ML language models. In the present disclosure, the term "language model" can refer to an ML-based language model (e.g., a language model that is implemented using a neural network or other ML architecture), unless stated otherwise. For example, unless stated otherwise, the "language model" encompasses large language models (LLMs).

A language model can use a neural network (typically a DNN) to perform natural language processing (NLP) tasks. A language model can be trained to model how words relate to each other in a textual sequence, based on probabilities. A language model may contain hundreds of thousands of learned parameters or, in the case of an LLM, can contain millions or billions of learned parameters or more. As non-limiting examples, a language model can generate text, translate text, summarize text, answer questions, write code (e.g., Python, JavaScript, or other programming languages), classify text (e.g., to identify spam emails), create content for various purposes (e.g., social media content, factual content, or marketing content), or create personalized content for a particular individual or group of individuals. Language models can also be used for AI assistants (e.g., virtual assistance).

A type of neural network architecture, referred to as a "transformer," can be used for language models. For example, the Bidirectional Encoder Representations from Transformers (BERT) model, Efficiently Learning an Encoder that Classifies Token Replacements Accurately (ELECTRA), Text-To-Text Transfer Transformer (T5), the Transformer-XL model, and the Generative Pre-trained Transformer (GPT) models are types of transformers. A transformer is a type of neural network architecture that uses self-attention mechanisms in order to generate predicted output based on input data that has some sequential meaning (i.e., the order of the input data is meaningful, which is the case for most text input). Although transformer-based language models are described herein, it should be understood that the present disclosure may be applicable to any ML-based language model, including language models based on other neural network architectures such as RNN-based language models.

Figure 13:
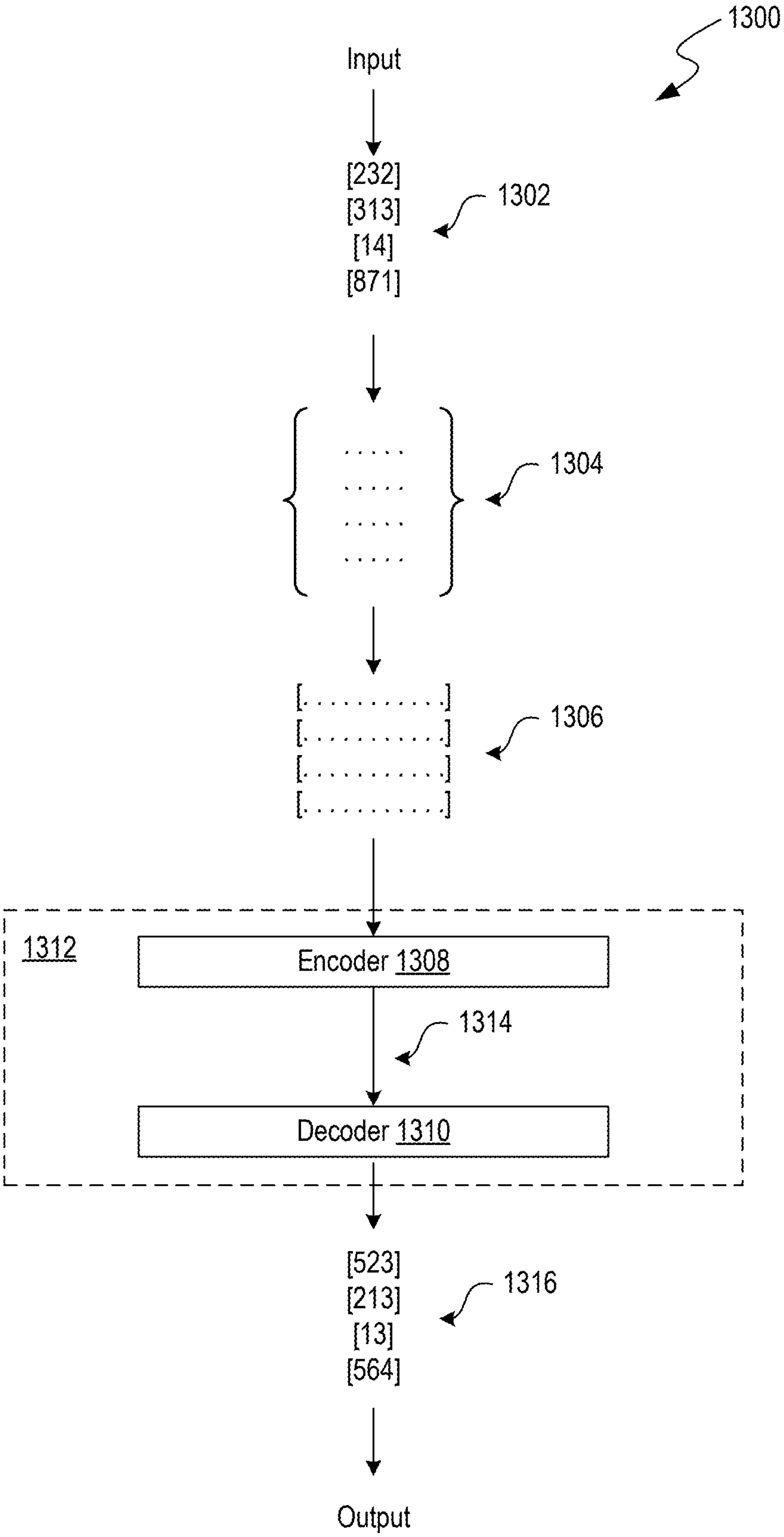
FIG. 13 is a block diagram of a transformer neural network, in accordance with some implementations of the present technology.

FIG. 13 is a block diagram 1300 of an example transformer 1312. A transformer is a type of neural network architecture that uses self-attention mechanisms to generate predicted output based on input data that has some sequential meaning (e.g., the order of the input data is meaningful, which is the case for most text input). Self-attention is a mechanism that relates different positions of a single sequence to compute a representation of the same sequence. Although transformer-based language models are described herein, the present disclosure may be applicable to any ML-based language model, including language models based on other neural network architectures such as RNN-based language models.

The transformer 1312 includes an encoder 1308 (which can include one or more encoder layers/blocks connected in series) and a decoder 1310 (which can include one or more decoder layers/blocks connected in series). Generally, the encoder 1308 and the decoder 1310 each include multiple neural network layers, at least one of which can be a self-attention layer. The parameters of the neural network layers can be referred to as the parameters of the language model.

The transformer 1312 can be trained to perform certain functions on a natural language input. Examples of the functions include generating new content, summarizing existing content, brainstorming ideas, writing a rough draft, fixing spelling and grammar, and translating content. Summarizing can include extracting key points or themes from an existing content in a high-level summary. Writing a rough draft can include generating writing in a particular style that could be useful as a starting point for the user's writing. The style can be identified as, e.g., a professional style (e.g., a medical report to be read by healthcare professionals) or a layman style (e.g., care instructions to be read by a subject). Fixing spelling and grammar can include correcting errors in an existing input text. Translating can include converting an existing input text into a variety of different languages. In some implementations, the transformer 1312 is trained to perform certain functions on other input formats than natural language input. For example, the input can include objects, images, audio content, or video content, or a combination thereof.

The transformer 1312 can be trained on a text corpus that is labeled (e.g., annotated to indicate verbs, nouns) or unlabeled. LLMs can be trained on a large unlabeled corpus. The term "language model," as used herein, can include an ML-based language model (e.g., a language model that is implemented using a neural network or other ML architecture), unless stated otherwise. Some LLMs can be trained on a large multi-language, multi-domain corpus to enable the model to be versatile at a variety of language-based tasks such as generative tasks (e.g., generating human-like natural language responses to natural language input).

FIG. 13 illustrates an example of how the transformer 1312 can process textual input data. Input to a language model (whether transformer-based or otherwise) typically is in the form of natural language that can be parsed into tokens. The term "token" in the context of language models and NLP has a different meaning from the use of the same term in other contexts such as data security. Tokenization, in the context of language models and NLP, refers to the process of parsing textual input (e.g., a character, a word, a phrase, a sentence, a paragraph) into a sequence of shorter segments that are converted to numerical representations referred to as tokens (or "compute tokens"). Typically, a token can be an integer that corresponds to the index of a text segment (e.g., a word) in a vocabulary dataset. Often, the vocabulary dataset is arranged by frequency of use. Commonly occurring text, such as punctuation, can have a lower vocabulary index in the dataset and thus be represented by a token having a smaller integer value than less commonly occurring text. Tokens frequently correspond to words, with or without white space appended. In some implementations, a token can correspond to a portion of a word.

For example, the word "greater" can be represented by a token for [great] and a second token for [er]. In another example, the text sequence "write a summary" can be parsed into the segments [write], [a], and [summary], each of which can be represented by a respective numerical token. In addition to tokens that are parsed from the textual sequence (e.g., tokens that correspond to words and punctuation), there can also be special tokens to encode non-textual information. For example, a [CLASS] token can be a special token that corresponds to a classification of the textual sequence (e.g., can classify the textual sequence as a list, a paragraph), an [EOT] token can be another special token that indicates the end of the textual sequence, other tokens can provide formatting information, etc.

In FIG. 13, a short sequence of tokens 1302 corresponding to the input text is illustrated as input to the transformer 1312. Tokenization of the text sequence into the tokens 1302 can be performed by some pre-processing tokenization module such as, for example, a byte-pair encoding tokenizer (the "pre" referring to the tokenization occurring prior to the processing of the tokenized input by the LLM), which is not shown in FIG. 13 for brevity. In general, the token sequence that is inputted to the transformer 1312 can be of any length up to a maximum length defined based on the dimensions of the transformer 1312. Each token 1302 in the token sequence is converted into an embedding vector 1306 (also referred to as "embedding 1306").

An embedding 1306 is a learned numerical representation (such as, for example, a vector) of a token that captures some semantic meaning of the text segment represented by the token 1302. The embedding 1306 represents the text segment corresponding to the token 1302 in a way such that embeddings corresponding to semantically related text are closer to each other in a vector space than embeddings corresponding to semantically unrelated text. For example, assuming that the words "write," "a," and "summary" each correspond to, respectively, a "write" token, an "a" token, and a "summary" token when tokenized, the embedding 1306 corresponding to the "write" token will be closer to another embedding corresponding to the "jot down" token in the vector space as compared to the distance between the embedding 1306 corresponding to the "write" token and another embedding corresponding to the "summary" token.

The vector space can be defined by the dimensions and values of the embedding vectors. Various techniques can be used to convert a token 1302 to an embedding 1306. For example, another trained ML model can be used to convert the token 1302 into an embedding 1306. In particular, another trained ML model can be used to convert the token 1302 into an embedding 1306 in a way that encodes additional information into the embedding 1306 (e.g., a trained ML model can encode positional information about the position of the token 1302 in the text sequence into the embedding 1306). In some implementations, the numerical value of the token 1302 can be used to look up the corresponding embedding in an embedding matrix 1304, which can be learned during training of the transformer 1312.

The generated embeddings 1306 are input into the encoder 1308. The encoder 1308 serves to encode the embeddings 1306 into feature vectors 1314 that represent the latent features of the embeddings 1306. The encoder 1308 can encode positional information (i.e., information about the sequence of the input) in the feature vectors 1314. The feature vectors 1314 can have very high dimensionality (e.g., on the order of thousands or tens of thousands), with each element in a feature vector 1314 corresponding to a respective feature. The numerical weight of each element in a feature vector 1314 represents the importance of the corresponding feature. The space of all possible feature vectors 1314 that can be generated by the encoder 1308 can be referred to as a latent space or feature space.

Conceptually, the decoder 1310 is designed to map the features represented by the feature vectors 1314 into meaningful output, which can depend on the task that was assigned to the transformer 1312. For example, if the transformer 1312 is used for a translation task, the decoder 1310 can map the feature vectors 1314 into text output in a target language different from the language of the original tokens 1302. Generally, in a generative language model, the decoder 1310 serves to decode the feature vectors 1314 into a sequence of tokens. The decoder 1310 can generate output tokens 1316 one by one. Each output token 1316 can be fed back as input to the decoder 1310 in order to generate the next output token 1316. By feeding back the generated output and applying self-attention, the decoder 1310 can generate a sequence of output tokens 1316 that has sequential meaning (e.g., the resulting output text sequence is understandable as a sentence and obeys grammatical rules). The decoder 1310 can generate output tokens 1316 until a special [EOT] token (indicating the end of the text) is generated. The resulting sequence of output tokens 1316 can then be converted to a text sequence in post-processing. For example, each output token 1316 can be an integer number that corresponds to a vocabulary index. By looking up the text segment using the vocabulary index, the text segment corresponding to each output token 1316 can be retrieved, the text segments can be concatenated together, and the final output text sequence can be obtained.

In some implementations, the input provided to the transformer 1312 includes instructions to perform a function on an existing text. The output can include, for example, a modified version of the input text and instructions to modify the text. The modification can include summarizing, translating, correcting grammar or spelling, changing the style of the input text, lengthening or shortening the text, or changing the format of the text (e.g., adding bullet points or checkboxes). As an example, the input text can include meeting notes prepared by a user and the output can include a high-level summary of the meeting notes. In other examples, the input provided to the transformer includes a query (e.g., a question or a request) to generate text. The output can include a response to the question, text associated with the query, or a list of ideas associated with the query. For example, the input can include the question "What is the weather like in San Francisco?" and the output can include a description of the weather in San Francisco. As another example, the input can include a request to brainstorm names for a flower shop and the output can include a list of relevant names.

Although a general transformer architecture for a language model and its theory of operation has been described above, this is not intended to be limiting. Existing language models include language models that are based only on the encoder of the transformer or only on the decoder of the transformer. An encoder-only language model encodes the input text sequence into feature vectors that can then be further processed by a task-specific layer (e.g., a classification layer). BERT is an example of a language model that can be considered to be an encoder-only language model. A decoder-only language model accepts embeddings as input and can use auto-regression to generate an output text sequence. Transformer-XL and GPT-type models can be language models that are considered to be decoder-only language models.

Because GPT-type language models tend to have a large number of parameters, these language models can be considered LLMs. An example of a GPT-type LLM is GPT-3. GPT-3 is a type of GPT language model that has been trained (in an unsupervised manner) on a large corpus derived from documents available online to the public. GPT-3 has a very large number of learned parameters (on the order of hundreds of billions), can accept a large number of tokens as input (e.g., up to 2,048 input tokens), and is able to generate a large number of tokens as output (e.g., up to 2,048 tokens). GPT-3 has been trained as a generative model, meaning that it can process input text sequences to predictively generate a meaningful output text sequence. ChatGPT is built on top of a GPT-type LLM and has been fine-tuned with training datasets based on text-based chats (e.g., chatbot conversations). ChatGPT is designed for processing natural language, receiving chat-like inputs, and generating chat-like outputs.

A computer system can access a remote language model (e.g., a cloud-based language model), such as ChatGPT or GPT-3, via a software interface (e.g., an API). Additionally or alternatively, such a remote language model can be accessed via a network such as the Internet. In some implementations, such as, for example, potentially in the case of a cloud-based language model, a remote language model can be hosted by a computer system that can include a plurality of cooperating (e.g., cooperating via a network) computer systems that can be in, for example, a distributed arrangement. Notably, a remote language model can employ multiple processors (e.g., hardware processors such as, for example, processors of cooperating computer systems). Indeed, processing of inputs by an LLM can be computationally expensive/can involve a large number of operations (e.g., many instructions can be executed/large data structures can be accessed from memory), and providing output in a required timeframe (e.g., real time or near real time) can require the use of a plurality of processors/cooperating computing devices as discussed above. Additional examples of remote language models include Google Cloud Natural Language, Microsoft Azure, Amazon Comprehend, and OpenAI, Inputs to an LLM can be referred to as a prompt, which is a natural language input that includes instructions to the LLM to generate a desired output. A computer system can generate a prompt that is provided as input to the LLM via an API. As described above, the prompt can optionally be processed or pre-processed into a token sequence prior to being provided as input to the LLM via its API. A prompt can include one or more examples of the desired output, which provides the LLM with additional information to enable the LLM to generate output according to the desired output. Additionally or alternatively, the examples included in a prompt can provide inputs (e.g., example inputs) corresponding to/as can be expected to result in the desired outputs provided. A one-shot prompt refers to a prompt that includes one example, and a few-shot prompt refers to a prompt that includes multiple examples. A prompt that includes no examples can be referred to as a zero-shot prompt.

Computer System

Figure 14:
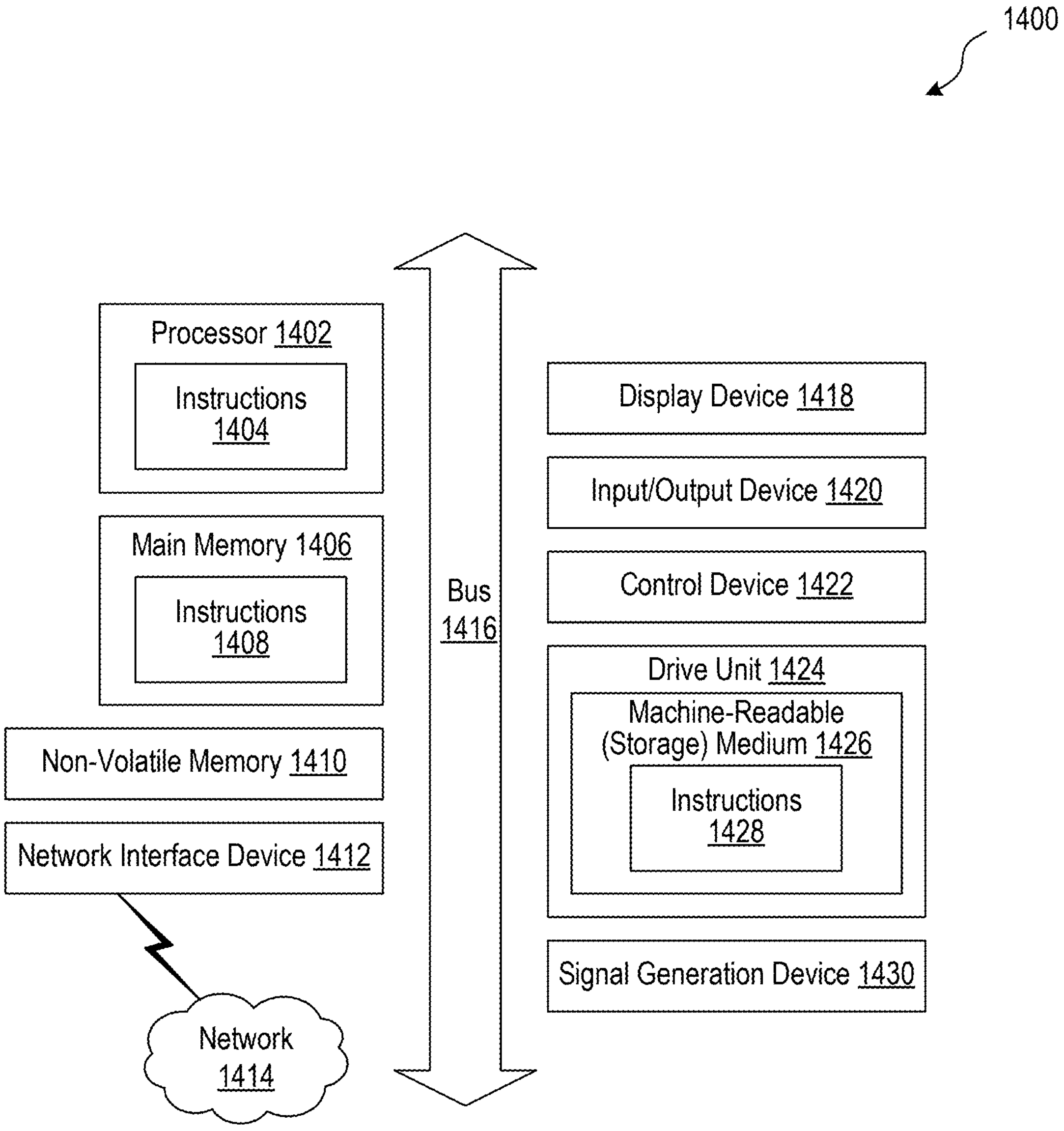
FIG. 14 is a block diagram that illustrates an example of a computer system in which at least some operations described herein can be implemented.

FIG. 14 is a block diagram that illustrates an example of a computer system 1400 in which at least some operations described herein can be implemented. As shown, the computer system 1400 can include: one or more processors 1402, main memory 1406, non-volatile memory 1410, a network interface device 1412, a display device 1418, an input/output device 1420, a control device 1422 (e.g., keyboard and pointing device), a drive unit 1424 that includes a machine-readable (storage) medium 1426, and a signal generation device 1430 that are communicatively connected to a bus 1416. The bus 1416 represents one or more physical buses and/or point-to-point connections that are connected by appropriate bridges, adapters, or controllers. Various common components (e.g., cache memory) are omitted from FIG. 14 for brevity. Instead, the computer system 1400 is intended to illustrate a hardware device on which components illustrated or described relative to the examples of the figures and any other components described in this specification can be implemented.

The computer system 1400 can take any suitable physical form. For example, the computer system 1400 can share a similar architecture as that of a server computer, personal computer (PC), tablet computer, mobile telephone, wearable electronic device, network-connected ("smart") device (e.g., a television or home assistant device), augmented reality/virtual reality (AR/VR) system (e.g., head-mounted display), or any electronic device capable of executing a set of instructions that specify action(s) to be taken by the computer system 1400. In some implementations, the computer system 1400 can be an embedded computer system, a system-on-chip (SOC), a single-board computer (SBC) system, or a distributed system such as a mesh of computer systems or include one or more cloud components in one or more networks. Where appropriate, one or more computer systems 1400 can perform operations in real time, near real time, or in batch mode.

The network interface device 1412 enables the computer system 1400 to mediate data in a network 1414 with an entity that is external to the computer system 1400 through any communication protocol supported by the computer system 1400 and the external entity. Examples of the network interface device 1412 include a network adapter card, a wireless network interface card, a router, an access point, a wireless router, a switch, a multilayer switch, a protocol converter, a gateway, a bridge, a bridge router, a hub, a digital media receiver, and/or a repeater, as well as all wireless elements noted herein.

The memory (e.g., main memory 1406, non-volatile memory 1410, machine-readable medium 1426) can be local, remote, or distributed. Although shown as a single medium, the machine-readable medium 1426 can include multiple media (e.g., a centralized/distributed database and/or associated caches and servers) that store one or more sets of instructions 1428. The machine-readable medium 1426 can include any medium that is capable of storing, encoding, or carrying a set of instructions for execution by the computer system 1400. The machine-readable medium 1426 can be non-transitory or comprise a non-transitory device. In this context, a non-transitory storage medium can include a device that is tangible, meaning that the device has a concrete physical form, although the device can change its physical state. Thus, for example, non-transitory refers to a device remaining tangible despite this change in state.

Although implementations have been described in the context of fully functioning computing devices, the various examples are capable of being distributed as a program product in a variety of forms. Examples of machine-readable storage media, machine-readable media, or computer-readable media include recordable-type media such as volatile and non-volatile memory devices 1410, removable flash memory, hard disk drives, optical disks, and transmission-type media such as digital and analog communication links.

In general, the routines executed to implement examples herein can be implemented as part of an operating system or a specific application, component, program, object, module, or sequence of instructions (collectively referred to as "computer programs"). The computer programs typically comprise one or more instructions (e.g., instructions 1404, 1408, 1428) set at various times in various memory and storage devices in computing device(s). When read and executed by the processor 1402, the instruction(s) cause the computer system 1400 to perform operations to execute elements involving the various aspects of the disclosure.

Remarks

The terms "example," "embodiment," and "implementation" are used interchangeably. For example, references to "one example" or "an example" in the disclosure can be, but not necessarily are, references to the same implementation; and such references mean at least one of the implementations. The appearances of the phrase "in one example" are not necessarily all referring to the same example, nor are separate or alternative examples mutually exclusive of other examples. A feature, structure, or characteristic described in connection with an example can be included in another example of the disclosure. Moreover, various features are described that can be exhibited by some examples and not by others. Similarly, various requirements are described that can be requirements for some examples but not other examples.

The terminology used herein should be interpreted in its broadest reasonable manner, even though it is being used in conjunction with certain specific examples of the invention. The terms used in the disclosure generally have their ordinary meanings in the relevant technical art, within the context of the disclosure, and in the specific context where each term is used. A recital of alternative language or synonyms does not exclude the use of other synonyms. Special significance should not be placed upon whether or not a term is elaborated or discussed herein. The use of highlighting has no influence on the scope and meaning of a term. Further, it will be appreciated that the same thing can be said in more than one way.

Unless the context clearly requires otherwise, throughout the description and the claims, the words "comprise," "comprising," and the like are to be construed in an inclusive sense, as opposed to an exclusive or exhaustive sense—that is to say, in the sense of "including, but not limited to." As used herein, the terms "connected," "coupled," or any variants thereof mean any connection or coupling, either direct or indirect, between two or more elements; the coupling or connection between the elements can be physical, logical, or a combination thereof. Additionally, the words "herein," "above," "below," and words of similar import can refer to this application as a whole and not to any particular portions of this application. Where context permits, words in the Detailed Description above using the singular or plural number may also include the plural or singular number, respectively. The word "or" in reference to a list of two or more items covers all of the following interpretations of the word: any of the items in the list, all of the items in the list, and any combination of the items in the list. The term "module" refers broadly to software components, firmware components, and/or hardware components.

While specific examples of technology are described above for illustrative purposes, various equivalent modifications are possible within the scope of the invention, as those skilled in the relevant art will recognize. For example, while processes or blocks are presented in a given order, alternative implementations can perform routines having ordered operations, or employ systems having blocks, in a different order, and some processes or blocks may be deleted, moved, added, subdivided, combined, and/or modified to provide alternative or sub-combinations. Each of these processes or blocks can be implemented in a variety of different ways. Also, while processes or blocks are at times shown as being performed in series, these processes or blocks can instead be performed or implemented in parallel, or can be performed at different times. Further, any specific numbers noted herein are only examples such that alternative implementations can employ differing values or ranges.

Details of the disclosed implementations can vary considerably in specific implementations while still being encompassed by the disclosed teachings. As noted above, particular terminology used when describing features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed herein, unless the Detailed Description above explicitly defines such terms. Accordingly, the actual scope of the invention encompasses not only the disclosed examples but also all equivalent ways of practicing or implementing the invention under the claims. Some alternative implementations can include additional elements to those implementations described above or include fewer elements.

Any patents and applications and other references noted above, and any that may be listed in accompanying filing papers, are incorporated herein by reference in their entireties, except for any subject matter disclaimers or disavowals, and except to the extent that the incorporated material is inconsistent with the express disclosure herein, in which case the language in this disclosure controls. Aspects of the invention can be modified to employ the systems, functions, and concepts of the various references described above to provide yet further implementations of the invention.

To reduce the number of claims, certain implementations are presented below in certain claim forms, but the applicant contemplates various aspects of an invention in other forms. For example, aspects of a claim can be recited in a means-plus-function form or in other forms, such as being embodied in a computer-readable medium. A claim intended to be interpreted as a means-plus-function claim will use the words "means for." However, the use of the term "for" in any other context is not intended to invoke a similar interpretation. The applicant reserves the right to pursue such additional claim forms either in this application or in a continuing application.

We claim:

1. At least one non-transitory, computer-readable storage medium comprising instructions recorded thereon, wherein the instructions when executed by at least one data processor of a system, cause the system to perform operations for providing artifact inspection using an artificial intelligence (AI) model, the operations comprising:

displaying, on a first portion of a graphical user interface, an AI-generated electronic artifact, wherein the AI-generated electronic artifact is created, by the AI model of an AI system, using an input comprising user data associated with a subject from a data source and a set of instructions, wherein the AI-generated electronic artifact indicates a user status for the subject created using the user data, wherein the user status identifies a user condition for the subject, and wherein the AI model is trained to identify the user condition for the subject using historical user data for subjects associated with historical user status classifications;

displaying, on a second portion of the graphical user interface, a confidence evaluation, wherein the confidence evaluation comprises a numerical value, generated by the AI system using the user data associated with the subject, historical user status data for the subject, and pre-defined guidelines, related to accuracy or quality of the user status or treatment of the subject;

responsive to a determination that the confidence evaluation satisfies an evaluation condition, and responsive to a first user input on an interface element associated with the user condition on the first portion of the graphical user interface, displaying, on a third portion of the graphical user interface, a portion of the user data that the AI system used for the AI-generated electronic artifact and a portion of the pre-defined guidelines used for generating the confidence evaluation, wherein the first portion, the second portion, and the third portion are displayed concurrently on the graphical user interface, and wherein displaying the AI-generated electronic artifact and the portion of the user data enables a user to inspect the accuracy of the AI-generated electronic artifact;

responsive to receiving a second user input, modifying the AI-generated electronic artifact including modifying the user status; and causing retraining of the AI model using the modified AI-generated electronic artifact including the modified user status.

2. The at least one non-transitory, computer-readable storage medium of claim 1, wherein the AI-generated electronic artifact comprises a utilization review providing information about care of the subject at a facility, and wherein the user data comprises medical data including a description of symptoms, medical status, treatment, and/or care instructions of the subject.

3. The at least one non-transitory, computer-readable storage medium of claim 2, wherein the confidence evaluation is generated by comparing the medical data associated with the subject to the pre-defined guidelines by associated entities, the facility, and/or officials, and wherein the confidence evaluation depicts whether medical status, treatment, and/or care instructions of the subject are in compliance with the pre-defined guidelines.

4. The at least one non-transitory, computer-readable storage medium of claim 3 wherein, in an instance that the utilization review indicates that medical status, treatment, and/or care instructions of the subject are not in compliance with the predefined guidelines, the portion of the medical data that the AI system used for the AI-generated electronic artifact comprises specific text extracted from the predefined guidelines that the medical status, treatment, and/or care instructions are not in compliance with.

5. The at least one non-transitory, computer-readable storage medium of claim 1, wherein the AI-generated electronic artifact comprises a description of the user status including medical status for the subject, and wherein the user data comprises medical data including a medical record associated with the subject.

6. The at least one non-transitory, computer-readable storage medium of claim 1, wherein displaying the portion of the user data comprises displaying an emphasis on the portion of the user data that the AI system used for the AI-generated electronic artifact.

7. The at least one non-transitory, computer-readable storage medium of claim 1, wherein the AI-generated electronic artifact comprises a medical report, clinical notes, a prescription, a treatment plan, a consent form, an insurance artifact, or a legal artifact.

8. The at least one non-transitory, computer-readable storage medium of claim 1, further comprising:

displaying, on the graphical user interface, an AI assistant interface element for inputting instructions that cause the AI system to modify the AI-generated electronic artifact, or generate additional content associated with the AI-generated electronic artifact.

9. A method for providing artifact inspection using an artificial intelligence (AI) model, the method comprising:

displaying, on a graphical user interface, an AI-generated electronic artifact, wherein the AI-generated electronic artifact is created, by the AI model of an AI system, using an input comprising medical data associated with a subject from a data source and a set of instructions, wherein the AI-generated electronic artifact indicates a medical status for the subject created using the medical data, wherein the medical status identifies a medical condition for the subject, and wherein the AI model is trained to identify the user condition for the subject using historical user data for subjects associated with historical user status classifications;

displaying, on the graphical user interface, a confidence evaluation, wherein the confidence evaluation comprises a numerical value, generated by the AI system using the medical data associated with the subjects and historical medical status data for the subject, and pre-defined guidelines, related to accuracy or quality of the medical status or treatment of the subject;

responsive to a determination that the confidence evaluation satisfies an evaluation condition, and responsive to a first user input on an interface element associated with the medical condition on the graphical user interface, displaying, on the graphical user interface, a portion of the medical data that the AI system used for the AI-generated electronic artifact and a portion of the pre-defined guidelines used for generating the confidence evaluation, wherein the first portion, the second portion, and the third portion are displayed concurrently on the graphical user interface, and wherein displaying the AI-generated electronic artifact and the portion of the medical data enables a user to inspect the accuracy of the AI-generated electronic artifact;

responsive to receiving a second user input, modifying the AI-generated electronic artifact including modifying the user status; and causing retraining of the AI model using the modified AI-generated electronic artifact including the modified user status.

10. The method of claim 9, wherein the AI-generated electronic artifact comprises a utilization review providing information about care of the subject at a facility, and wherein the medical data comprises a description of the subject's symptoms, medical status, treatment, and/or care instructions.

11. The method of claim 10, wherein the confidence evaluation is generated by comparing the medical data associated with the subject to the pre-defined guidelines by associated entities, the facility, and/or officials, and wherein the confidence evaluation depicts whether the subject's medical status, treatment, and/or care instructions are in compliance with the pre-defined guidelines.

12. The method of claim 11, wherein, in an instance that the utilization review indicates that the subject's medical status, treatment, and/or care instructions are not in compliance with the pre-defined guidelines, the portion of the medical data that the AI system used for the AI-generated electronic artifact comprises specific text extracted from the pre-defined guidelines that the medical status, treatment, and/or care instructions are not in compliance with.

13. The method of claim 9, wherein the AI-generated electronic artifact comprises a description of the medical status for the subject, and wherein the medical data comprises a medical record associated with the subject.

14. The method of claim 9, wherein displaying the portion of the medical data comprises displaying an emphasis on the portion of the medical data that the AI system used for the AI-generated electronic artifact.

15. The method of claim 9, wherein the AI-generated electronic artifact comprises a medical report, clinical notes, a prescription, a treatment plan, a consent form, an insurance artifact, or a legal artifact.

16. A system for providing artifact inspection using artificial intelligence (AI) models, the system comprising:

at least one hardware processor; and at least one non-transitory memory storing instructions, which, when executed by the at least one hardware processor, cause the system to:

display, on a graphical user interface, an AI-generated electronic artifact, wherein the AI-generated electronic artifact is created, by the AI model of an AI system, using an input comprising medical data associated with a subject from a data source and a set of instructions, wherein the AI-generated electronic artifact indicates a medical status for the subject created using the medical data, and wherein the medical status identifies a medical condition for the subjects and wherein the AI model is trained to identify the user condition for the subject using historical user data for subjects associated with historical user status classifications;

display, on the graphical user interface, a confidence evaluation, wherein the confidence evaluation comprises a numerical value, generated by the AI system using the medical data associated with the subjects and historical medical status data for the subject, and pre-defined guidelines, related to accuracy or quality of the medical status or treatment of the subject;

responsive to a determination that the confidence evaluation satisfies an evaluation condition, and responsive to a first user input on an interface element associated with the medical condition on the graphical user interface, display, on the graphical user interface, a portion of the medical data that the AI system used for the AI-generated electronic artifact and a portion of the pre-defined guidelines used for generating the confidence evaluation, wherein the first portion, the second portion, and the third portion are displayed concurrently on the graphical user interface, and wherein displaying the AI-generated electronic artifact and the portion of the medical data enables a user to inspect the accuracy of the AI-generated electronic artifact;

responsive to receiving a second user input, modify the AI-generated electronic artifact including modifying the user status; and cause retraining of the AI model using the modified AI-generated electronic artifact including the modified user status.

17. The system of claim 16, wherein the AI-generated electronic artifact comprises a utilization review providing information about care of the subject at a facility, and wherein the medical data comprises a description of the subject's symptoms, medical status, treatment, and/or care instructions.

18. The system of claim 17, wherein the confidence evaluation is generated by comparing the medical data associated with the subject to the pre-defined guidelines by associated entities, the facility, and/or officials, and wherein the confidence evaluation depicts whether the subject's medical status, treatment, and/or care instructions are in compliance with the pre-defined guidelines.

19. The system of claim 18, wherein, in an instance that the utilization review indicates that the subject's medical status, treatment, and/or care instructions are not in compliance with the pre-defined guidelines the portion of the medical data that the AI system used for the AI-generated electronic artifact comprises specific text extracted from the pre-defined guidelines that the medical status, treatment, and/or care instructions are not in compliance with.

20. The system of claim 17, wherein the AI-generated electronic artifact comprises a description of the medical status for the subject, and wherein the medical data comprises a medical record associated with the subject.

* * * * *